(12) United States Patent
Costello et al.

(10) Patent No.: US 9,525,093 B2
(45) Date of Patent: Dec. 20, 2016

(54) INFRARED ATTENUATING OR BLOCKING LAYER IN OPTICAL PROXIMITY SENSOR

(71) Applicant: Avago Technologies General IP (Singapore) Pte. Ltd., Singapore (SG)

(72) Inventors: James Costello, Singapore (SG); Rani Ramamoorthy Saravanan, Singapore (SG); Boon Keat Tan, Singapore (SG)

(73) Assignee: Avago Technologies General IP (Singapore) Pte. Ltd., Singapore (SG)

(*) Notice: Subject to any disclaimer, the term of this patent is extended or adjusted under 35 U.S.C. 154(b) by 272 days.

(21) Appl. No.: 13/934,132

(22) Filed: Jul. 2, 2013

(65) Prior Publication Data
US 2013/0292706 A1    Nov. 7, 2013

Related U.S. Application Data

(63) Continuation-in-part of application No. 13/098,436, filed on Apr. 30, 2011, now Pat. No. 8,957,380, which
(Continued)

(51) Int. Cl.
*G01J 1/42* (2006.01)
*H01L 31/167* (2006.01)
(Continued)

(52) U.S. Cl.
CPC ............ *H01L 31/167* (2013.01); *B05D 1/322* (2013.01); *G01D 5/24433* (2013.01);
(Continued)

(58) Field of Classification Search
CPC .... H01L 31/167; H01L 31/173; G01D 11/305; G01D 5/34715; G01D 5/24433; B05D 1/322; G01S 17/026; G01S 7/4813; G01V 8/12; G01N 21/552; G01J 1/42; H03K 2017/9455; H03K 2217/94108
See application file for complete search history.

(56) References Cited

U.S. PATENT DOCUMENTS 5,155,777 A    10/1992  Angelopoulos et al.
5,367,393 A    11/1994  Ohara et al.
(Continued)

FOREIGN PATENT DOCUMENTS

CN    1743886    8/2006
CN    1832217    9/2006
(Continued)

OTHER PUBLICATIONS

"A4 Masking Sheet—A4 Masking Sheet", Downloaded from website: <http://www.stix2.com.au/a4-masking-sheet-13/a4-masking-sheet.html> 2012, Product Description 2012.
(Continued)

*Primary Examiner* — Yara B Green

(57) ABSTRACT

An optical proximity sensor is provided that comprises an infrared light emitter an infrared light detector, a first molded optically transmissive infrared light pass component disposed over and covering the light emitter and a second molded optically transmissive infrared light pass component disposed over and covering the light detector. Located in-between the light emitter and the first molded optically transmissive infrared light pass component, and the light detector and the second molded optically transmissive infrared light pass component is a gap. Layers of infrared opaque, attenuating or blocking material are disposed on at least some of the external surfaces forming the gap to substantially attenuate or block the transmission of undesired direct, scattered or reflected light between the light emitter and the light detector, and thereby minimize optical crosstalk and interference between the light emitter and the light detector.

20 Claims, 29 Drawing Sheets

Related U.S. Application Data is a continuation-in-part of application No. 12/495,739, filed on Jun. 30, 2009, now Pat. No. 8,779,361.

(51) Int. Cl.

| | | |
|---|---|---|
| *H01L 31/173* | (2006.01) | |
| *B05D 1/32* | (2006.01) | |
| *G01D 11/30* | (2006.01) | |
| *G01S 17/02* | (2006.01) | |
| *G01S 7/481* | (2006.01) | |
| *H03K 17/94* | (2006.01) | |
| *G01D 5/244* | (2006.01) | |
| *G01D 5/347* | (2006.01) | |
| *G01V 8/12* | (2006.01) | |
| *G01N 21/552* | (2014.01) | |
| *H03K 17/945* | (2006.01) | |

(52) U.S. Cl.
CPC ....... *G01D 5/34715* (2013.01); *G01D 11/305* (2013.01); *G01S 7/4813* (2013.01); *G01S 17/026* (2013.01); *H01L 31/173* (2013.01); *H03K 17/941* (2013.01); *G01J 1/42* (2013.01); *G01N 21/552* (2013.01); *G01V 8/12* (2013.01); *H03K 2017/9455* (2013.01); *H03K 2217/94108* (2013.01)

(56) References Cited

U.S. PATENT DOCUMENTS

| | | |
|---|---|---|
| 5,567,953 A | 10/1996 | Horinouchi et al. |
| 5,675,143 A | 10/1997 | Heimlicher |
| 5,760,390 A | 6/1998 | Vezzalini et al. |
| 5,811,797 A | 9/1998 | Kobachi et al. |
| 6,064,062 A | 5/2000 | Bohn |
| 6,135,816 A | 10/2000 | Mashiyama et al. |
| 6,180,881 B1 | 1/2001 | Isaak |
| 6,364,706 B1 | 4/2002 | Ando et al. |
| 6,572,410 B1 | 6/2003 | Volstorf et al. |
| 6,635,955 B2 | 10/2003 | Scheidle |
| 6,674,653 B1 | 1/2004 | Valentine |
| 6,677,934 B1 | 1/2004 | Blanchard |
| 6,740,862 B2 | 5/2004 | Paritsky et al. |
| 6,771,671 B1 | 8/2004 | Fields et al. |
| 6,835,923 B2 | 12/2004 | Hamalainen et al. |
| 6,855,933 B2 | 2/2005 | Stone et al. |
| 6,885,300 B1 | 4/2005 | Johnston et al. |
| 7,026,710 B2 | 4/2006 | Coyle et al. |
| 7,172,126 B2 | 2/2007 | Schmidt et al. |
| 7,229,295 B2 | 6/2007 | Ice et al. |
| 7,256,483 B2 | 8/2007 | Eppler et al. |
| 7,258,264 B2 | 8/2007 | Ice et al. |
| 7,277,012 B2 | 10/2007 | Johnston et al. |
| 7,289,142 B2 | 10/2007 | Silverbrook |
| 7,348,536 B2 | 3/2008 | Bockel et al. |
| 7,387,033 B2 | 6/2008 | Qing et al. |
| 7,387,907 B2 | 6/2008 | Hsu et al. |
| 7,427,806 B2 | 9/2008 | Arndt et al. |
| 7,485,818 B2 | 2/2009 | Chou |
| 7,510,888 B2 | 3/2009 | Guenther et al. |
| 7,514,666 B2 | 4/2009 | Yee et al. |
| 7,582,513 B2 | 9/2009 | Kroeninger et al. |
| 7,675,132 B2 | 3/2010 | Waitl et al. |
| 7,755,029 B2 | 7/2010 | Tang et al. |
| 7,767,485 B2 | 8/2010 | Ogawa et al. |
| 7,851,246 B2 | 12/2010 | Camacho |
| 8,026,472 B2 | 9/2011 | Arnold |
| 8,031,174 B2 | 10/2011 | Hamblin et al. |
| 8,097,852 B2 | 1/2012 | Yao |
| 8,143,608 B2 | 3/2012 | Yao et al. |
| 8,207,517 B2 | 6/2012 | Wang et al. |
| 8,275,922 B2 | 9/2012 | Barrett et al. |
| 8,420,999 B2 | 4/2013 | Costello et al. |
| 8,575,537 B2 | 11/2013 | Yao et al. |
| 2002/0172472 A1 | 11/2002 | Nelson et al. |
| 2004/0065894 A1 | 4/2004 | Hashimoto et al. |
| 2005/0088900 A1 | 4/2005 | Chan |
| 2005/0199786 A1 | 9/2005 | Yoshida et al. |
| 2006/0016994 A1 | 1/2006 | Basoor et al. |
| 2006/0017069 A1 | 1/2006 | Bergmann |
| 2006/0022212 A1 | 2/2006 | Waitl et al. |
| 2006/0022215 A1 | 2/2006 | Arndt et al. |
| 2006/0045530 A1 | 3/2006 | Lim et al. |
| 2006/0049533 A1 | 3/2006 | Kamoshita |
| 2006/0118807 A1 | 6/2006 | Ives |
| 2007/0045524 A1 | 3/2007 | Rains |
| 2007/0072321 A1 | 3/2007 | Sherrer et al. |
| 2007/0085157 A1 | 4/2007 | Fadell |
| 2007/0246646 A1* | 10/2007 | Lum .................. G01D 5/34715 250/231.13 |
| 2008/0006762 A1 | 1/2008 | Fadell et al. |
| 2008/0011939 A1 | 1/2008 | Yee et al. |
| 2008/0011940 A1 | 1/2008 | Zhang et al. |
| 2008/0012033 A1 | 1/2008 | Arndt |
| 2008/0030878 A1* | 2/2008 | Saxena .................. G02B 3/04 359/721 |
| 2008/0049210 A1 | 2/2008 | Takaoka |
| 2008/0116379 A1 | 5/2008 | Teder |
| 2008/0118241 A1 | 5/2008 | TeKolste et al. |
| 2008/0165115 A1 | 7/2008 | Herz et al. |
| 2008/0173790 A1 | 7/2008 | Cheng et al. |
| 2008/0173963 A1 | 7/2008 | Hsu et al. |
| 2008/0179503 A1 | 7/2008 | Camargo et al. |
| 2008/0197376 A1 | 8/2008 | Bert et al. |
| 2008/0223934 A1 | 9/2008 | Havens |
| 2008/0265266 A1 | 10/2008 | Bogner et al. |
| 2008/0296478 A1 | 12/2008 | Hernoult |
| 2008/0308738 A1 | 12/2008 | Li et al. |
| 2008/0308917 A1 | 12/2008 | Pressel et al. |
| 2009/0027652 A1 | 1/2009 | Chang et al. |
| 2009/0057799 A1 | 3/2009 | Chan et al. |
| 2009/0101804 A1 | 4/2009 | Le |
| 2009/0129783 A1 | 5/2009 | Ori et al. |
| 2009/0159900 A1 | 6/2009 | Basoor |
| 2009/0168088 A1 | 7/2009 | Rosenblatt |
| 2009/0267173 A1 | 10/2009 | Takahashi et al. |
| 2010/0030039 A1 | 2/2010 | Lamego et al. |
| 2010/0171027 A1 | 7/2010 | Yun |
| 2010/0246771 A1 | 9/2010 | Hawver et al. |
| 2010/0282951 A1 | 11/2010 | Costello et al. |
| 2010/0327164 A1 | 12/2010 | Costello et al. |
| 2011/0024627 A1 | 2/2011 | Yao |
| 2011/0057102 A1 | 3/2011 | Yao |
| 2011/0057104 A1 | 3/2011 | Yao et al. |
| 2011/0057129 A1 | 3/2011 | Yao et al. |
| 2011/0121181 A1 | 5/2011 | Costello |
| 2011/0204233 A1 | 8/2011 | Costello et al. |
| 2011/0297831 A1* | 12/2011 | Yao et al. .................. 250/338.4 |
| 2012/0035511 A1* | 2/2012 | Schoenbach et al. ............ 601/3 |
| 2012/0070145 A1* | 3/2012 | Wong et al. .................. 396/439 |
| 2012/0086015 A1* | 4/2012 | Kyono .................. B82Y 20/00 257/76 |
| 2012/0146073 A1 | 6/2012 | Phipps et al. |
| 2012/0160994 A1 | 6/2012 | Costello et al. |
| 2012/0306816 A1* | 12/2012 | Bridger ........................ 345/175 |
| 2013/0037831 A1* | 2/2013 | Rudmann .............. H01L 25/167 257/88 |

FOREIGN PATENT DOCUMENTS

| | | |
|---|---|---|
| EP | 1455564 | 9/2004 |
| EP | 2019293 | 1/2009 |
| GB | 2486000 | 6/2012 |
| JP | 63308973 | 12/1988 |
| JP | H05-11469 | 2/1993 |
| JP | 11242926 | 9/1999 |
| JP | 2006-114737 | 4/2006 |
| JP | 2006-261380 | 9/2006 |
| JP | 2008-181097 | 8/2008 |
| JP | 2008-265187 | 11/2008 |
| JP | 2009032571 | 2/2009 |
| JP | 2009-137528 | 6/2009 |

(56) References Cited

FOREIGN PATENT DOCUMENTS

| WO | WO-2006045531 | 5/2006 |
|---|---|---|
| WO | WO 2008/078806 | 7/2008 |
| WO | WO-2009/072786 | 6/2009 |
| WO | WO-2012068213 | 5/2012 |

OTHER PUBLICATIONS

"Agilent HSDL-9100 Miniature Surface-Mount Proximity Sensor Data Sheet", Dec. 21, 2007.
"Altera 40/100 Gigabit Ethernet", *Altera Corporation Data Sheet Copyright* 1995-2012, 3 pages 2012.
"Altera's 10-Gbps Ethernet (XAUI) Solution", *Altera Corporation Data Sheet*, Copyright 1995-2012, 2 pages 2012.
"APDS-9900 and APDS-9901 Digital Proximity and Ambient Light Sensor", Data Sheet, Mar. 23, 2011.
"Nordson Ink-Dot I.D. System", *Nordson Corporation Data Sheet*2012, 2 pages.
"SerialLite II Protocol", *Altera Reference Manual*Oct. 2005, 84 pages 2005.
Agilent Technologies, "Agilent HSDL-9100 Miniature Surface-Mount Proximity Sensor Data Sheet", Aug. 26, 2004.
Avago Technologies, "APDS-9005 Miniature Surface-Mount Ambient Light Photo Sensor", Data Sheet, Jan. 2007.
Avago Technologies, "APDS-9101—Integrated Reflective Sensor", *Data Sheet* 2007.
Avago Technologies, "APDS-9700 Signal Conditioning IC for Optical Proximity Sensors", Jan. 4, 2008.
Avago Technologies, "Avago Technologies Announces Ultra-Thin Integrated Ambient Light and Proximity Sensor Module for Use in Mobile Phones", *Wireless Design and Development* Nov. 27, 2009.
Avago Technologies, "HSDL-9100—Surface-Mount Proximity Sensor", *Data Sheet* 2006.
Avago Technologies, "Integrated Ambinet Light and Proximity Sensor Prelim Datasheet", *APDS-9800* Mar. 2, 2009.
Avago Technologies, "Integrated Optical Proximity Sensors", *APDS 9120, Data Sheet* Mar. 3, 2009.
AZ Optics, "Device Debuts as the World's Best-Performing Integrated Light/Proximity Sensor", Nov. 11, 2008.
Costello, et al, "U.S. Appl. No. 12/495,739", *Optical Proximity Sensor Package with Molded Infrared Light Rejection Barrier and Infrared Pass Components* Jun. 30, 2009.
IDES—The Plastic Web, , "Si Photo Diode Chip", Dec. 19, 2007.
Ishihara, et al., "A Dual Face Package Using a Post with Wire Components: Novel Structure for PoP Wafer Level CSP and Compact Image Sensor Package", *Electronic Components and Technology Conference* 2008 , 1093-1098.
Khamal, Ibrahim , "Infra-Red Proiximilty Sensor (II)", Apr. 4, 2008.
Losee, et al., "A 1/3 Format Image Sensor with Refractory Metal Light Shield for Color Video Applications", *Solid State Circuits Conference, Digest of Technical Papers, 36th ISSCC, IEEE International Volume*. Feb. 1989 , 90-91.
Morgavi, Paul , "Panasonic Print Head Technology and Market Applications", *IMI Europe, Digital Printing Conferences 2007, Presentation*, Nov. 7-9, 2007, 24 pages 2007.
Nitto Denko Corporation, , "Technical Data Sheet", *NT-8506* 2001.
Nitto Denko Corporation, , "Technical Data Sheet", *NT-MB-IRL3801* 2008.
PENCHEM Technologies Data Sheet, , "PEMCHEM OP 580", *IR Filter Optoelectronic Epoxy* Apr. 2009.
PENCHEM Technologies Data Sheet, , "PENCHEM OP 579", *IR Pass Optoelectronic Epoxy* Apr. 2009.
Tan, et al., "U.S. Appl. No. 12/623,767", *Infrared Proximity Sensor Package with Improved Crosstalk Isolation*, filed Nov. 23, 2009, 30 pages.
TYNTEK, "Data Sheet for AlGaAs/GaAs Infrared Chip", *TK116IRA* Nov. 2006.
TYNTEK, "Data Sheet for AlGaAs/GaAs Infrared Chip", *TK 114IRA* Mar. 2004.
TYNTEK, "Si Photo-Diode Chip—TK043PD Data Sheet", Dec. 19, 2007.
XYDAR, "G-930—Solvay Advanced Polymers—Liquid Crystal Polymer Data Sheet", reproduced from website at www.ides.com/grades/ds/E22219.htm on Dec. 17, 2007.

* cited by examiner

INFRARED ATTENUATING OR BLOCKING LAYER IN OPTICAL PROXIMITY SENSOR

RELATED APPLICATIONS

This application claims priority and other benefits from, and is a continuation-in-part of, U.S. patent application Ser. No. 13/098,436 filed Apr. 30, 2011 entitled "Infrared Attenuating or Blocking Layer in Optical Proximity Sensor", which is a continuation-in-part of U.S. patent application Ser. No. 12/495,739 filed Jun. 30, 2009 entitled "Optical Proximity Sensor Package with Molded Infrared Light Rejection Barrier and Infrared Pass Components". Each patent application identified above is incorporated here by reference in its entirety.

BACKGROUND

Optical proximity sensors, such as the AVAGO TECHNOLOGIES™ HSDL-9100 surface-mount proximity sensor, the AVAGO TECHNOLOGIES™ APDS-9101 integrated reflective sensor, the AVAGO TECHNOLOGIES™ APDS-9120 integrated optical proximity sensor, and the AVAGO TECHNOLOGIES™ APDS-9800 integrated ambient light and proximity sensor, are known in the art. Such sensors typically comprise an integrated high efficiency infrared emitter or light source and a corresponding photodiode or light detector, and are employed in a large number of hand-held electronic devices such as mobile phones, Personal Data Assistants ("PDAs"), laptop and portable computers, portable and handheld devices, amusement and vending machines, industrial automation machinery and equipment, contactless switches, sanitary automation machinery and equipment, and the like.

Referring to FIG. 1, there is shown a prior art optical proximity sensor 10 comprising infrared light emitter 16, light emitter driving circuit 51, light detector or photodiode 12, light detector sensing circuit 53, metal housing or shield 18 with apertures 55 and 57, and object to be sensed 60. Light rays 15 emitted by emitter 16 and reflected as light rays 19 from object 60 (which is in relatively close proximity to optical proximity sensor 10) are detected by photodiode 12 and thereby provide an indication that object 60 is close or near to sensor 10.

As further shown in FIG. 1, optical proximity sensor 10 further comprises metal housing or shield 18 formed of metal and comprising apertures 55 and 57 located over light emitter 16 and light detector 12, respectively, such that at least a first portion of light 15 emitted by light detector 12 passes through aperture 55, and at least a second portion of the first portion 19 of light reflected from object 50 in proximity to sensor 10 passes through aperture 57 for detection by light detector 12. As shown, metal housing or shield 18 may further comprise first and second modules 61 and 63 within which light emitter 16 and light detector 12 are disposed, respectively. The first and second modules 61 and 63 comprise adjoining optically opaque metal inner sidewalls 25 to provide optical isolation between first and second modules 61 and 63.

Many optical proximity sensors generally include a metal shield, such as shield or housing 18 of the type shown in FIG. 1, to provide optical isolation between light emitter 16 and light detector or photodiode 12 so that undesired optical cross-talk between emitter 16 and detector 12 is minimized. See, for example, the Data Sheets corresponding to the AVAGO TECHNOLOGIES™ APDS-9120 Integrated Optical Sensors Preliminary Datasheet and the AVAGO TECHNOLOGIES™ APDS-9800 Integrated Ambient Light and Proximity Sensors Preliminary Datasheet, each of which is hereby incorporated by reference herein, each in its respective entirety.

The amount of reflected, diffracted or refracted IR radiation and undesired crosstalk or interference between light emitter 16 and light detector 12 may also be exacerbated by the presence of a window disposed above sensor 10, which in some applications is provided as part of a portable or other type of electronic device in which proximity sensor 10 is housed and mounted.

FIG. 2 shows a prior art optical proximity sensor 10 with metal shield or housing 18. The optical proximity sensor shown in FIG. 2 is an AVAGO TECHNOLOGIES™ APDS-9120 Integrated Optical Proximity Sensor, which contains a molded plastic substrate 11 upon which are mounted LED 16 and light detector or photodiode 12. Single-piece metal shield 18 covers LED 16 and light detector or photodiode 12 and contains a downwardly projecting light barrier 65 disposed therebetween (not shown in FIG. 2). Electrical contacts 17 provide a means to establish electrical connections between proximity sensor 10 and external devices. In the APDS-9120 optical proximity sensor, metal shield 18 is formed and thinned using conventional metal stamping techniques, and is affixed to the underlying plastic substrate 11 by gluing. The APDS-9120 sensor has an areal footprint of only 4 mm by 4 mm, and thus is quite small.

FIG. 3 shows a prior art optical proximity sensor 10 with a more complicated metal shield or housing 18 than that of FIG. 2. The optical proximity sensor shown in FIG. 3 is an AVAGO TECHNOLOGIES™ APDS-9800 Integrated Ambient Light and Proximity Sensor, which contains a printed circuit board ("PCB") substrate 11 upon which are mounted LED 16, light detector or photodiode 12, and ambient light sensor 14. The one-piece metal shield 18 covers LED 16, light detector or photodiode 12, and ambient light sensor 14 and contains a downwardly projecting light barrier 65 disposed therebetween. In the APDS-9800 optical proximity sensor, metal shield 18, being of a considerably more complicated shape and geometry than that of FIG. 2, is formed and thinned using more advanced progressive metal stamping techniques, and must be hand-fitted and attached to the underlying PCB by gluing to ensure proper alignment and fit.

As will now be seen, at least some optical proximity sensors of the prior art rely upon the use of an externally mounted metal shield 18, which is required to reduce the amount of crosstalk or interference that might otherwise occur between LED 16 and light detector 12, as well as to help increase the detection distance of the device. Metal shields 18 are quite small, however, making them difficult to manufacture in high volumes, and thus expensive to fabricate. Such metal shields 18 also generally require expensive automated equipment to attach same to sensors 10 in a mass production setting. Moreover, the quality of metal shields 18 often varies, and issues commonly arise with suppliers being unable to meet the tight dimensional tolerances required for such small devices. Metal shields 18 can also detach from sensor 10, thereby adding another failure point for sensor 10.

What is need is an optical proximity sensor design that eliminates the need to include a metal shield 18, but which retains high crosstalk and interference rejection characteristics so that an optical proximity sensor can be provided that features improved performance, lower cost, increased manufacturability and improved reliability.

BRIEF DESCRIPTION OF THE DRAWINGS

Illustrative embodiments by way of examples, not by way of limitation, are illustrated in the drawings. Throughout the description and drawings, similar reference numbers may be used to identify similar elements. The drawings are for illustrative purpose to assist understanding and may not be drawn per actual scale.

DETAILED DESCRIPTION

Figure 1:
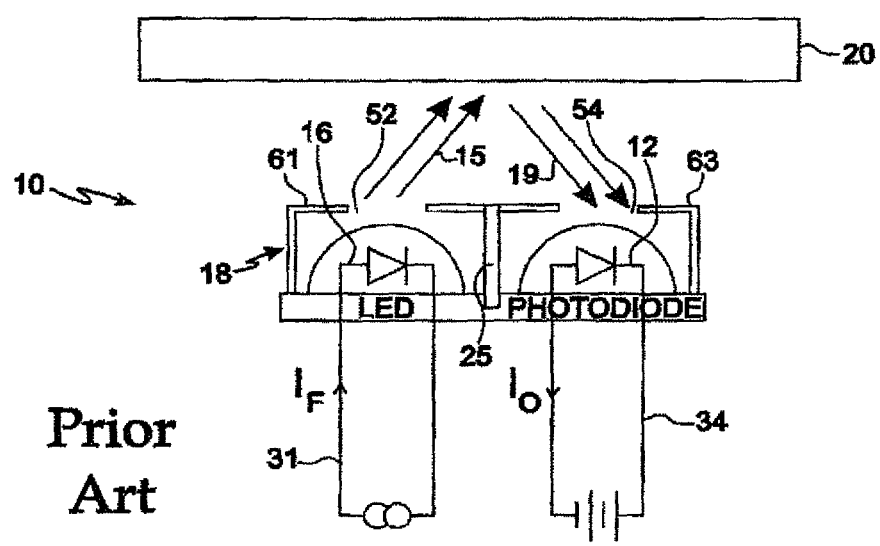
FIG. 1 shows a prior art optical proximity sensor and associated circuitry.
Figure 2:
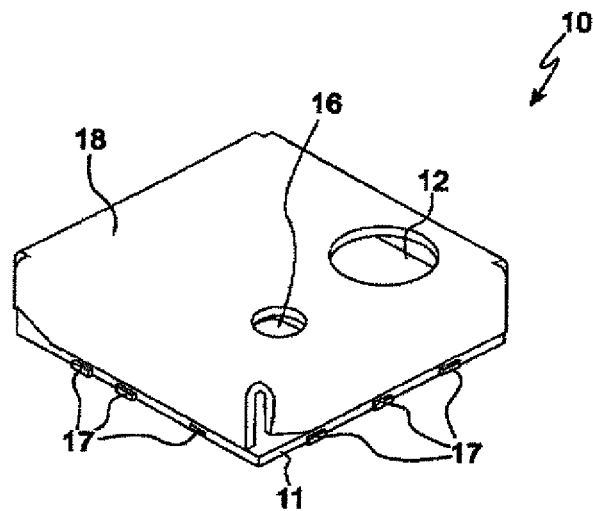
FIG. 2 shows a prior art optical proximity sensor with a metal shield or housing.
Figure 3:
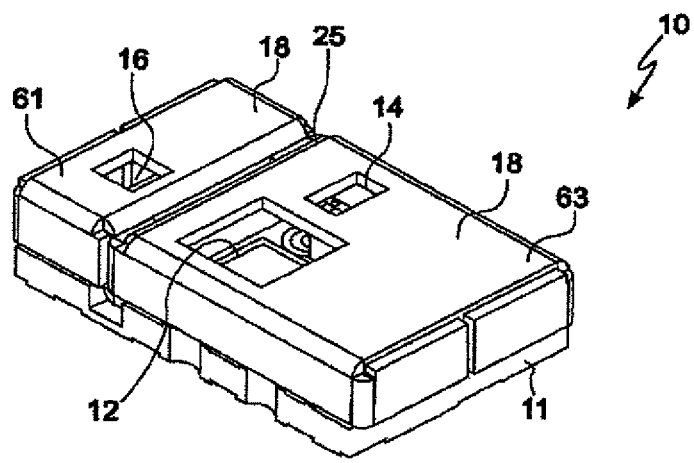
FIG. 3 shows a prior art optical proximity sensor with a more complicated metal shield or housing than that shown in FIG. 2.
Figure 4:
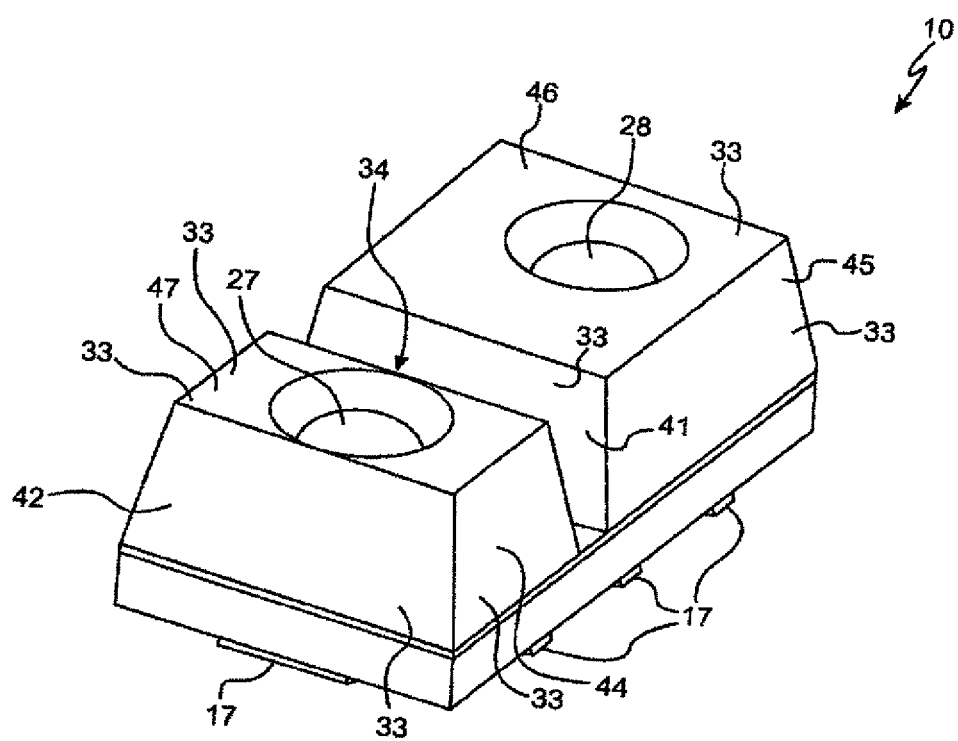
FIG. 4 shows a top perspective view of one embodiment of an optical proximity sensor.
Figure 5:
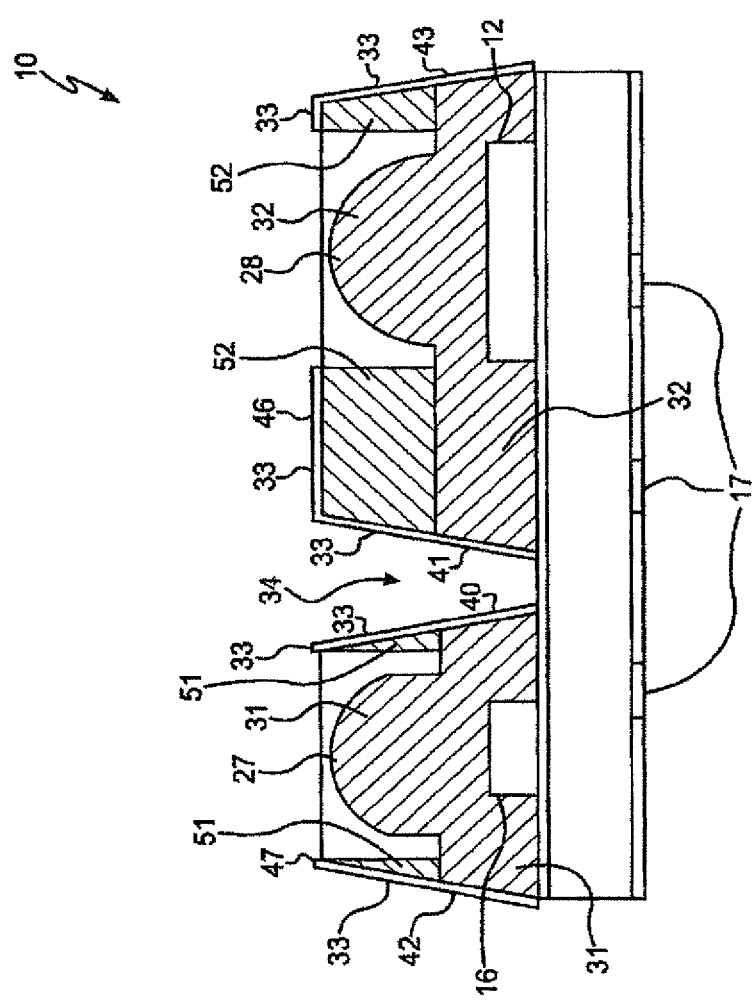
FIG. 5 shows a cross-sectional view of the optical proximity sensor of FIG. 4.

Referring now to FIGS. 4 and 5, there are shown top perspective and cross-sectional views of one embodiment of an optical proximity sensor 10 comprising light emitter 16 mounted on substrate 11 and separated from light detector 12 by gap 34, optically transmissive materials 31 and 32 (or first and second components 31 and 32), which are preferably single mold two-part epoxy or transfer molding compounds, and infrared opaque, light attenuating or blocking layers 33 disposed over at least portions of components 31 and 32 located adjacent to gap 34, and preferably disposed elsewhere on other external surfaces of sensor 10.

Light rays transmitted through optically transmissive material or first component 31 and originating from light emitter 16, and other reflected, diffracted or refracted IR radiation, might, but for the presence of layers 33, leak across to light detector 12 through optically transmissive material 32 (or second component 32), which would manifest itself as undesired crosstalk or interference between light emitter 16 and light detector 12 and thereby degrade the performance of proximity sensor 10.

FIGS. 4 and 5 show one embodiment of sensor 10 that provides solutions to the problems described above in the Background section, where metal barrier 25 is eliminated altogether. Continuing to refer to FIGS. 4 and 5, there is shown optical proximity sensor 10 comprising infrared light emitter 16 (which is operably connected to and driven by a light emitter driving circuit), and light detector 12 (which is operably connected to and driven by a detector sensing circuit, the details of which are not shown in FIG. 7). In one embodiment, a first molded optically transmissive infrared light pass component 31 is disposed over and covers at least portions of light emitter 16 and a second molded optically transmissive infrared light pass component 32 is disposed over and covers at least portions of light detector 12. Optical lenses 27 and 29, preferably formed of the same material, and formed at the same time during the manufacturing process as first and second molded optically transmissive infrared light pass components 31 and 32, are disposed over light emitter 16 and light detector 12, respectively. Located in-between light emitter 16 and first molded optically transmissive infrared light pass material and first component 31, and light detector 12 and second molded optically transmissive infrared light pass material and second component 32, is gap 34 (preferably an air gap, but which may also be a gap filled with a suitable material) and infrared or optically opaque, attenuating or blocking layers 33 disposed on, by way of example, external surfaces 40, 41, 42, 43, 44, 45, 46 and 47 of first and second components 31 and 32, where layers 33 preferably comprise an optically opaque non-transmissive infrared light barrier component or additive. At least a first portion of light 15 emitted by light detector 16 passes through first component 31, and at least a second portion 19 of the first portion of light 15 reflected from an object of interest in proximity to proximity sensor 10 passes through second component 32 for detection by light detector 12. Infrared or optically opaque, attenuating or blocking layers 33 substantially attenuate or block the transmission of undesired direct, scattered or reflected light between light emitter 16 and light detector 12, and thereby minimize optical crosstalk and interference between light emitter 16 and light detector 12.

According to one embodiment, first and second molded optically transmissive infrared light pass components 31 and 32 are formed using an infrared-pass and optically transmissive transfer molding compound such as NITTO DENKO™ NT-8506 clear transfer molding compound or PENCHEM Technologies™ OP 579 infrared pass optoelectronic epoxy. Other suitable optically transmissive epoxies, plastics, polymers or other materials may also be employed. In some embodiments, and as discussed in further detail below, optically transmissive infrared light pass components 31 and 32 are molded during the same manufacturing step, or may be molded separately. See Technical Data Sheet NT-8506 entitled "Clear Transfer Molding Compound NT-8506" dated 2001 and PENCHEM OP 579 IR Pass Optoelectronic Epoxy Data Sheet, Revision 1, dated April, 2009, both of which documents are hereby incorporated by reference herein, each in its respective entirety.

Referring now to FIG. 5, there are shown third and fourth components 51 and 52, which are located above first and second components 31 and 32. Third and fourth components 51 and 52 are preferably molded onto the top surfaces of first and second components 31 and 32, and according to one embodiment may comprise an infrared-blocking, filtering or cutting transfer molding compound such as NITTO DENKO198 NT-MB-IRL3801 two-part epoxy resin material or PENCHEM Technologies™, OP 580 infrared filter optoelectronic epoxy, either of which preferably contains an amount of an infrared cutting material that has been selected by the user to achieve acceptable infrared light blocking performance while minimizing the amount of such infrared cutting material employed to keep costs to a minimum. Other suitable optically non-transmissive epoxies, plastics, polymers or other materials may also be employed to form third and fourth components 51 and 52, as may optically-transparent materials in the event that layers 33 are found to provide adequate levels of optical isolation. See Technical Data Sheet NT-MB-IRL3801 published by DENKO™ dated 2008 and PENCHEM OP 580 IR Filter Optoelectronic Epoxy Data Sheet, Revision 1, dated April, 2009, both of which documents are hereby incorporated by reference herein, each in its respective entirety.

Figure 7:
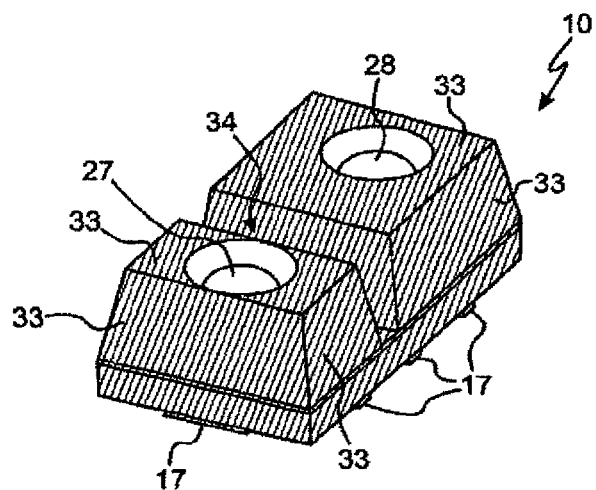

Continuing to refer to FIG. 5, infrared opaque, light attenuating or blocking layers 33 are disposed over at least some of the external surfaces of first and second components 31 and 32, and optionally over at least portions of third and fourth components 51 and 52, preferably, although not necessarily, after first and second components 31 and 32, and third and fourth components 51 and 52 have been formed in place atop substrate 11 and over light emitter 16 and light detector 12. It is especially important that at least portions of external surfaces 40 and 41 adjacent gap 34 be covered with layers 33 so as to effectively block the transmission of infrared light across gap 34. Better yet, and as shown in FIG. 7, most external surfaces of sensor 10 are covered with layers 33 so as to minimize undesired crosstalk between emitter 16 and detector 12. Note that substrate 11 may be, by way of example, a printed circuit board (PCB), lead frame, or the like. Additionally, and according to one embodiment, after first and second components 31 and 32, and third and fourth components 51 and 52 have been formed in place by, for example, molding, gap 34 is formed by cutting a groove corresponding to gap 34 between first component 31 and third component 51 on the one hand, and second component 32 and fourth component 52 on the other hand. This grove cutting and gap forming step may be carried out during the singulation process, more about which is said below. Note that external surfaces 40 and 41 preferably have angles ranging between about 2 degrees and 30 degrees from vertical to help facilitate the application of layers 33 thereon.

Figure 6:
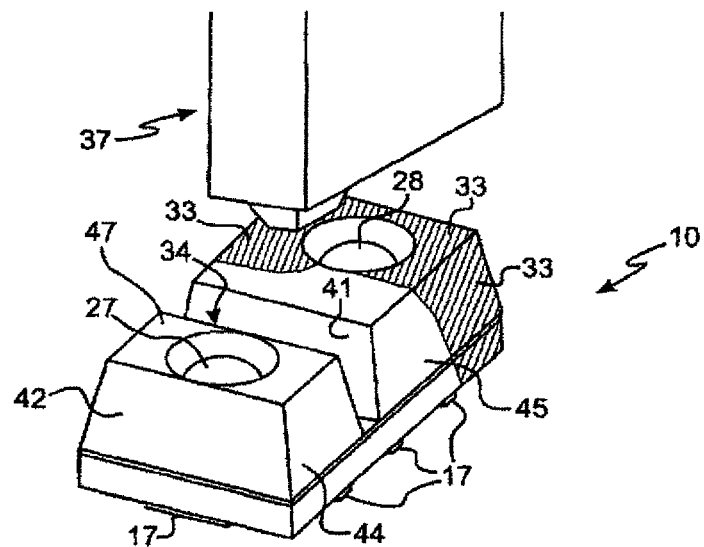
FIGS. 6 and 7 show one method of applying layers 33 to external surfaces of a proximity sensor.

Referring now to FIGS. 6 and 7, there is shown one embodiment of a method for applying layers 33 to the external surfaces of sensor 10. Ink dispenser 37 is configured to spray an appropriate optically opaque infrared ink controllably over sensor 10 such that, for example, lenses 27 and 28 and electrical contacts 17 are not covered with layers 33. In. FIG. 6, the spraying operation is in progress and not yet completed. In FIG. 7, the spraying operation has been completed and most the external surfaces of sensor 10 have been covered with layers 33. According to some embodiments, layers 33 may be formed, for example, using suitable infrared opaque, attenuating or blocking paints, inks, dyes or other materials. Such materials may further comprise infrared cut or blocking additives. Layers 33 may be formed to have thicknesses ranging between about 2 microns and about 100 microns, or between about 10 microns and about 40 microns. Layers 33 may be applied to at least portions of the external surfaces of sensor 10 by any one or more of spraying, dipping, brushing, rolling, electrodepositing, and sputtering a suitable infrared light attenuating material thereon.

Figure 8:
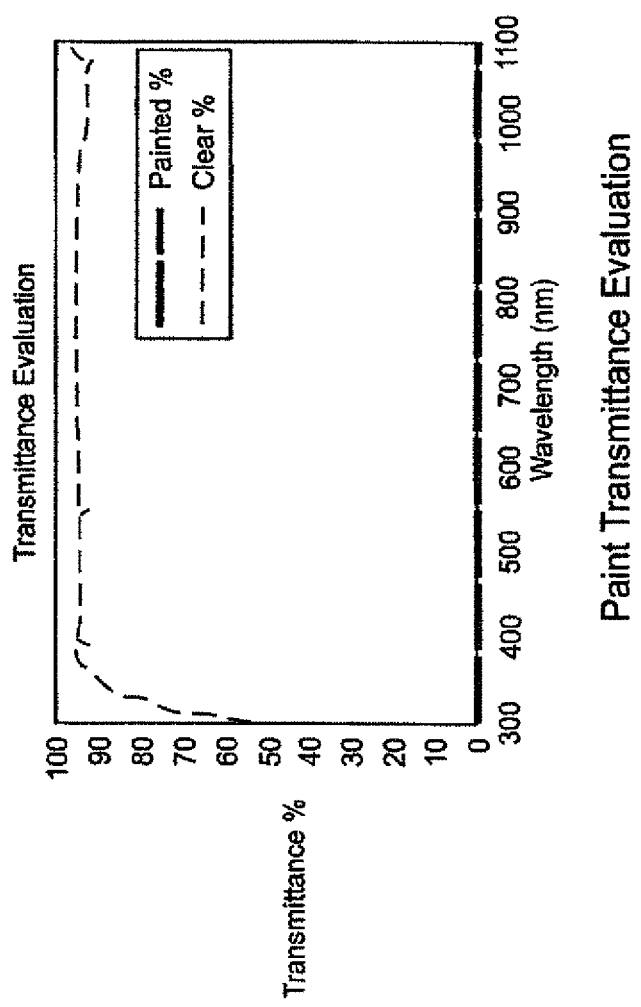
FIG. 8 shows comparative optical isolation results obtained with an optical proximity sensor having optically attenuating ink applied and not applied to the external surfaces thereof.

One material suitable for application on the external surfaces of sensor 10 to form layers 33 is an ink manufactured in Singapore under the name "DIC SCREEN INK," product Number 21-S175, having the designation "Safire Black." This material was tested by applying same to the external surfaces of an AVAGO TECHNOLOGIES APDS-9900 proximity sensor manufactured in accordance with the foregoing description regarding the first, second, third and fourth components, and the application of layers 33 to the external surfaces thereof. A Data Sheet entitled "APDS-9900 AND APDS-9901 Digital Proximity and Ambient Light Sensor" published by Avago Technologies on Mar. 23, 2011 is hereby incorporated by reference herein, in its entirety. FIG. 8 shows results obtained with and without layers 33 applied to sensor 10. FIG. 8 shows that the effectiveness of layers 33 in providing optical isolation is quite dramatic.

Figure 9:
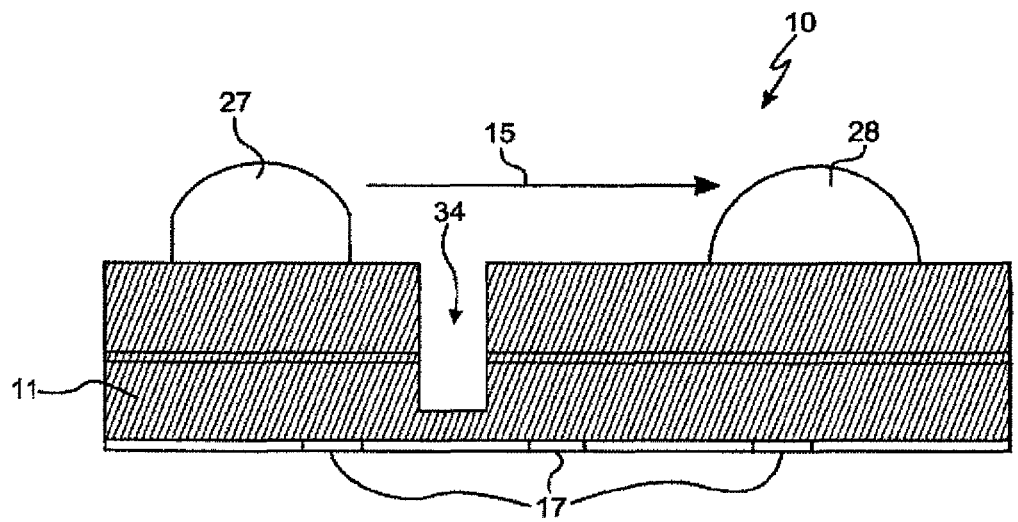
FIGS. 9 and 10 show two different test proximity sensors.
Figure 10:
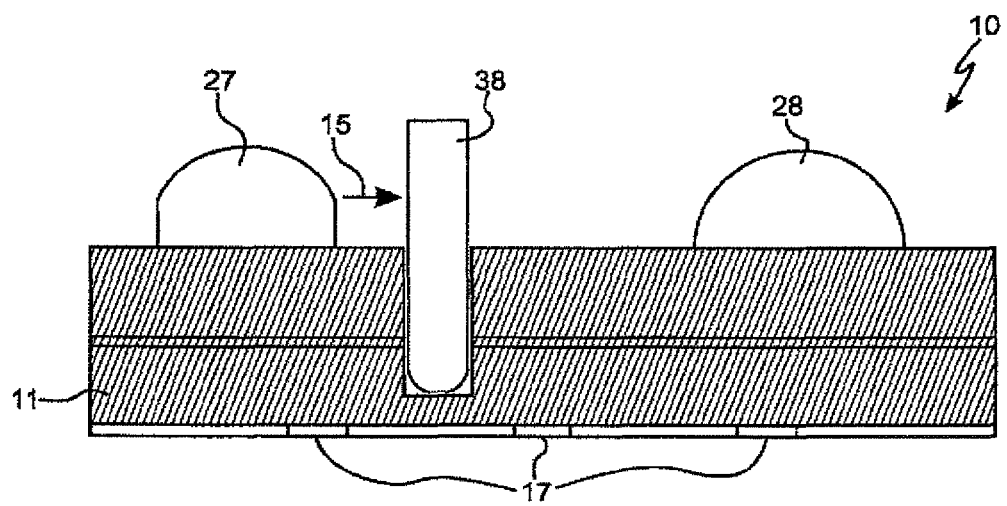

FIGS. 9 and 10 show examples of test devices that were built in accordance with the above teachings, where layers 33 comprising "DIC SCREEN INK" were applied to the external surfaces of sensor 10 (excepting electrical contacts 17 and lenses 27 and 28). In the example device of FIG. 9, where no additional light barrier 38 was disposed between lens 27 and lens 28, crosstalk was measured at 299 counts (which according to APDS-9900 specifications should not exceed a count of 200), and signal values of 684 counts were measured ((which according to APDS-9900 specifications range between 440 and 640). In the example device of FIG. 10, additional light barrier 38 was disposed between lens 27 and lens 28, and crosstalk was measured at 152 counts (which according to APDS-9900 specifications should not exceed a count of 200), and signal values of 619 counts were measured (which according to APDS-9900 specifications should range between 440 and 640). These test results further confirm the efficacy and effectiveness of layers 33 in providing optical isolation between various portions of sensor 10.

Figure 11:
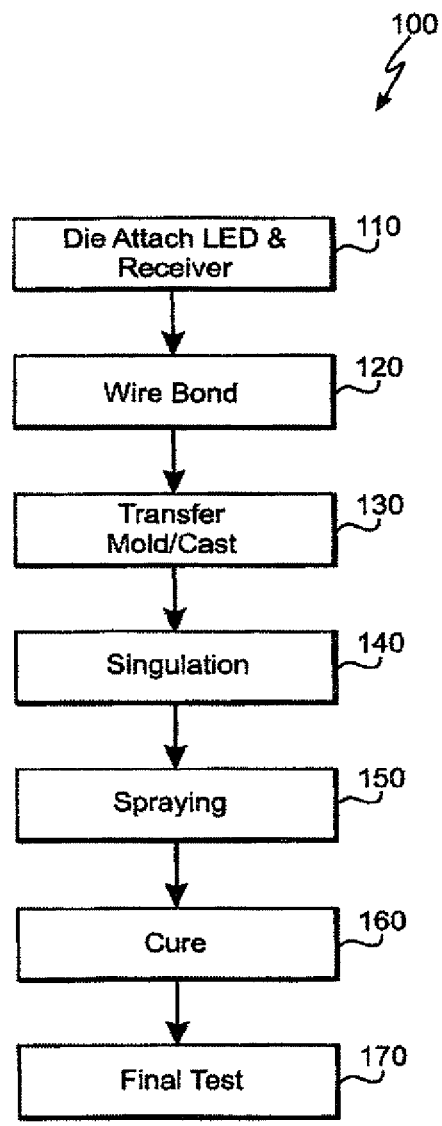
FIG. 11 shows a method of making an optical proximity sensor according to one embodiment.

FIG. 11 illustrates a method 100 of making optical proximity sensor 10 according to one embodiment. As shown in FIG. 11, the light emitter and detector dice are attached to substrate 11 in step 110 using epoxy. In one embodiment substrate 11 is a printed circuit board or PCB, or may be a lead frame. At step 120, the light emitter and detector dice are wire-bonded to substrate 11. Next, in step 130, first and second components comprising optically transmissive infrared light pass components 31 and 32 are molded over light emitter 16 and light detector 12 using a suitable infrared-pass and optically transmissive transfer molding compound. In an optional step not shown in FIG. 11, an integrated circuit is attached to substrate 11, where integrated circuit 35 contains the electronic circuitry required to drive light emitter 16, and process output signals provided by light detector 12, and optionally contains an ambient light sensor. Such an integrated circuit 35 is preferably wire-bonded to substrate 11. At step 130, substantially optically non-transmissive infrared light components 51 and 52 may also be molded onto the top surfaces of first and second optically transmissive infrared light pass components 31 and 32, and are preferably configured and compatible in respect of molded first and second optically-transmissive components 31 and 32 to bond thereto without delaminating under normal operating conditions.

Note that in FIG. 11, at steps 110 through 170, a plurality of PCB substrates 11 may be provided on a panel with light emitter dice and light detector dice attached and then wire-bonded thereto. Light emitter dice and light detector dice are then overmolded using cast or transfer molding techniques with a suitable optically-transmissive material to form first and second optically transmissive infrared light pass components 31 and 32 and lenses 27 and 28. Mold runners may be provided to facilitate the distribution of the various molding materials to the various PCB substrates. Light emitter driver integrated circuits containing integrated ambient light sensors may also be attached to such PCB substrates 11, and then wirebonded thereto. The entire PCB panel may be sheet cast using a suitable infrared cut, filter or block material to form substantially optically non-transmissive infrared third and fourth components 51 and 52 atop first and second optically transmissive infrared light pass components 31 and 32. Individual proximity sensors 10 may then be singulated by, for example, using sawing techniques well known to those skilled in the art, where mold runners are also removed. See step 140 in FIG. 11.

At step 150 in FIG. 11, layers 33 are applied to the desired external surfaces of the proximity sensor by, for example, spraying. Optionally, prior to spraying at step 170, one or more removeable masking layers may be formed or placed over first and second masking regions of first and second external surfaces of first and second light pass components. The spraying step is followed by curing at step 160. Optionally following the curing at step 160, in the case where removeable masking layers may be employed, such removeable masking layers may be removed. Subsequently, there may be final testing of sensor 10 at step 170.

FIGS. 12A-12G are a sequential series of figures showing another embodiment of applying layers to external surfaces 41, 42, 44, 45, 46 and 47 for proximity sensor 10. The substrate of the proximity sensor 10 may comprise a lead frame having electrical contacts 17, which may be used to provide electrical connections between proximity sensor 10 and external devices. In another embodiment, the substrate may be a printed circuit board. As discussed previously herein, for the proximity sensor 10 a light detector may be mounted on the substrate, and the light detector may be spaced apart from the light emitter on the substrate.

As mentioned previously herein, first light pass component may be formed integral with first lens 27 over at least portions of the light emitter. First light pass component may comprise first external surfaces 42, 44, 47. Second light pass component may be formed integral with second lens 28 over at least portions of the light detector. Second light pass component may comprise second external surfaces 41, 45, 46. First and second lenses 27 and 28, may be formed of the same material, and may be formed at the same time during the manufacturing process as first and second light pass components are disposed over the light emitter and the light detector, respectively.

At least portions of the first and second light pass components may be separated by a gap 34. For the sensor 10, its light emitter may comprise a semiconductor emitter die having a major emitter surface, and its light detector may comprise a semiconductor detector die having a major detector surface. The gap 34 separating the first and second light pass components may comprise a groove extending inwardly past at least one of the major emitter surface and the major detector surface to a base extremity of the groove.

Figure 12A:
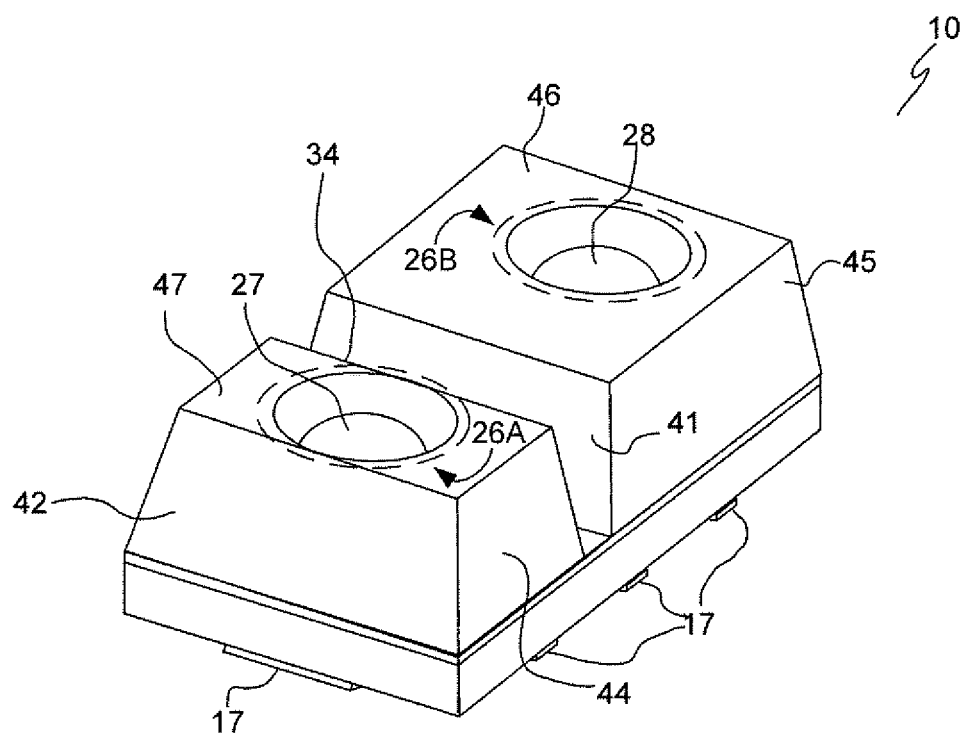
FIGS. 12A-12G are a sequential series of figures showing another embodiment of applying layers to external surfaces of a proximity sensor.
Figure 12B:
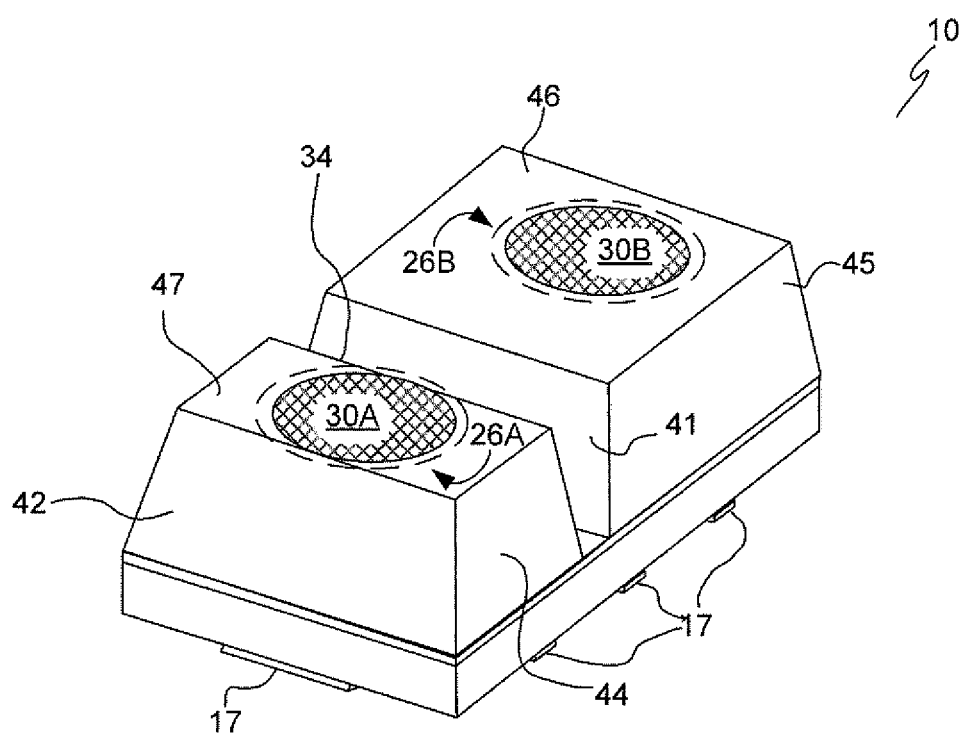

As shown in FIGS. 12A and 12B, notional dashed lines highlight and encircle first and second masking regions 26A, 266 of the first and second external surfaces 46, 47. As shown in FIG. 12B, one or more layers of removable masking material 30A, 30B may be formed and/or placed over first and second masking regions 26A, 26B of the first and second external surfaces 46, 47. For example, one suitable removable masking material may be Ultra Light-Weld™ 9-20479-B peelable solder mask, which may be available from Dymax Corporation, having a principal place of business at 318 Industrial Lane, Torrington, Conn. 06790 USA. As another example, another suitable removable masking material may be Chemask™ W water soluable solder mask, which may be available from ITW Chemtronics, having a principal place of business at 8125 Cobb Center Drive, Kennesaw, Ga. 30152 USA.

The one or more layers of removable masking material 30A, 30B may be formed and/or placed in various ways. For example, a pressurized dispenser with a suitably sized applicator tip may be used for forming and/or placing the one or more layers of removable masking material 30A, 30B over the first and second masking regions 26A, 266 of the first and second external surfaces 46, 47. Alternatively or additionally, a silk screening or screen printing process may be used for forming and/or placing the one or more layers of removable masking material 30A, 30B over the first and second masking regions 26A, 26B of the first and second external surfaces 46, 47. The removable masking layer may be dried and/or cured in place. For example, in some cases ultra-violate light may be used for curing.

Figure 12C:
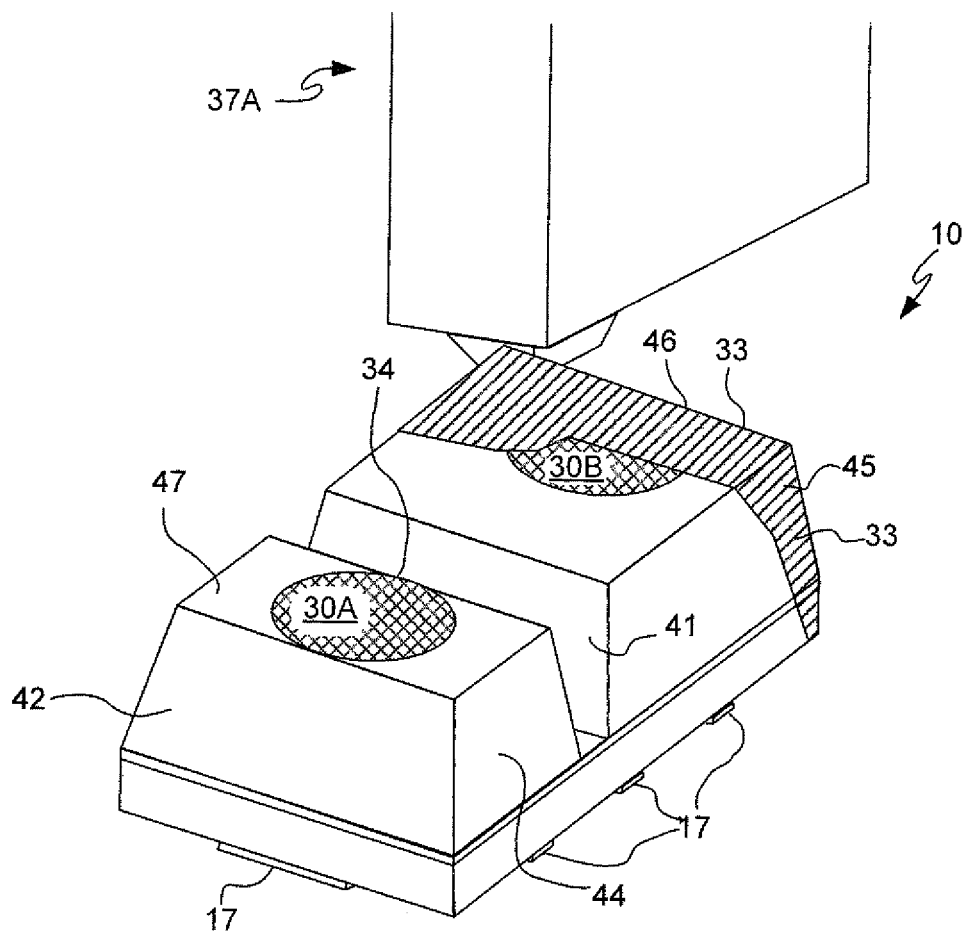
Figure 12D:
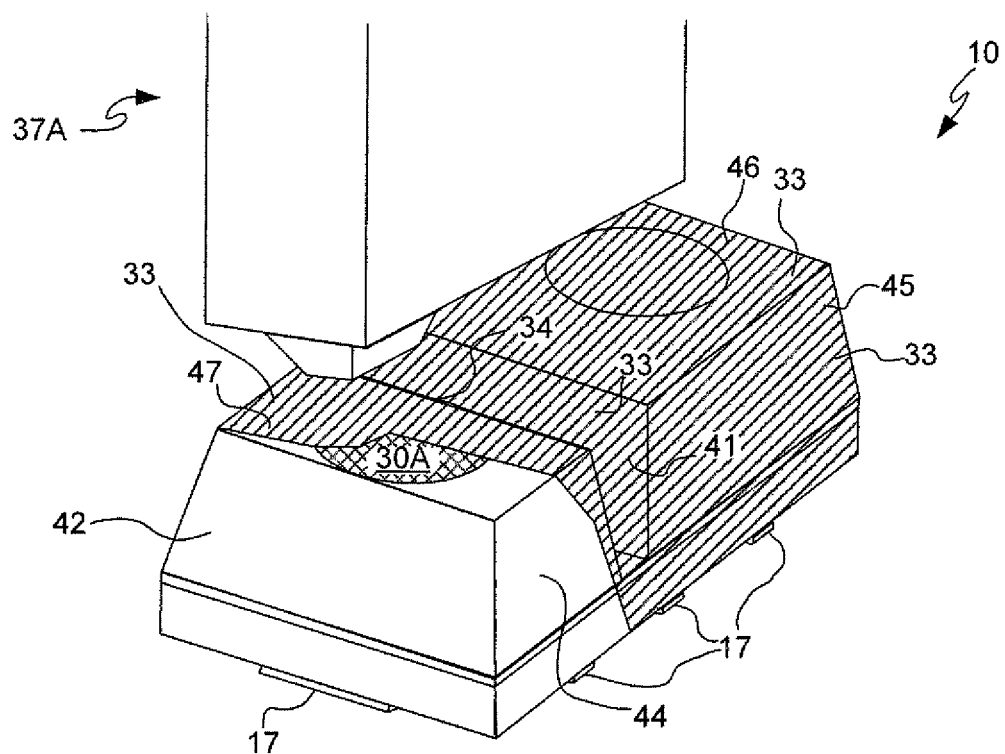
Figure 12E:
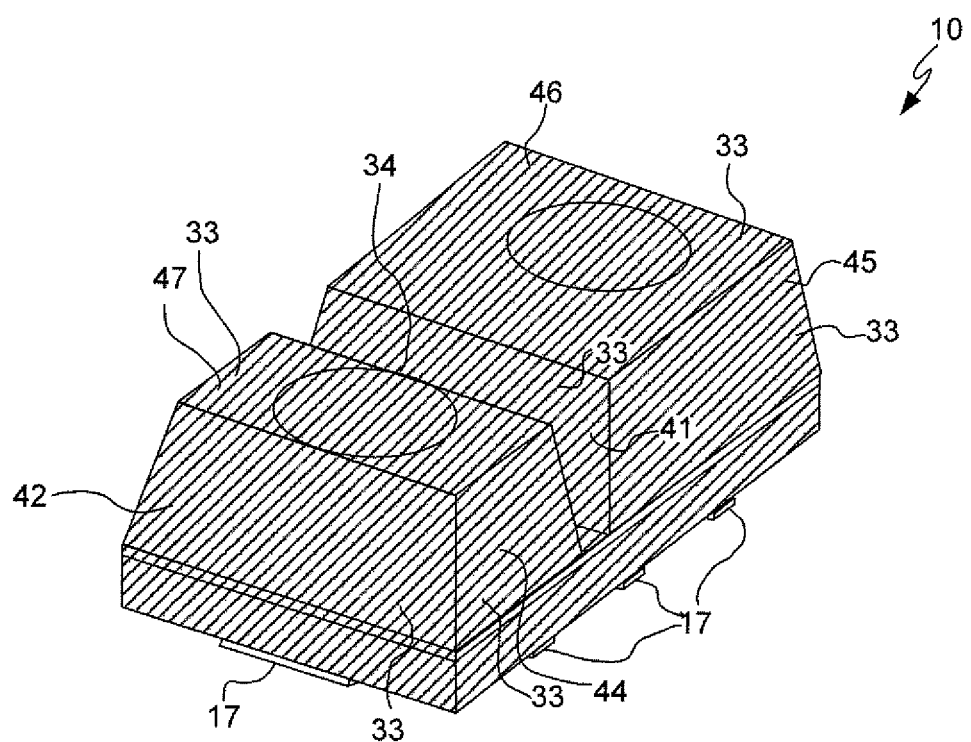

FIGS. 12C, 12D and 12E show initial, intermediate and final stages of forming and/or placing a layer 33 of light attenuating or blocking material over at least portions of the first and second external surfaces 41, 46, 47 located adjacent to the gap 34. The layer 33 of light attenuating material may be formed and/or placed over substantially most of the first and second external surfaces 46, 47. The layer 33 of light attenuating material may be one of a paint, an ink and a dye. The light attenuating material may be configured to attenuate or block substantially the transmission of undesired direct, scattered or reflected light between the light emitter and the light detector and thereby may substantially avoid optical crosstalk and/or interference between the light emitter and the light detector.

Ink dispenser 37A may be configured to spray an appropriate optically opaque infrared ink in one or more layers 33 over sensor, while first and second lenses 27, 28 (and/or first and second masking regions 26A, 26B) may be shielded therefrom by the one or more layers of masking material 30A, 30B. In other words, the light attenuating material may be formed and/or placed over the one or more removeable masking layers 30A, 30B, so that the one or more removeable masking layers 30A, 30B may be sandwiched between at least a portion of the layer 33 of light attenuating material and the first and second masking regions 26A, 26B.

In some embodiments, such as what is shown in FIGS. 12C and 12D, the ink dispenser may move in a scanning motion as it sprays. As shown in sequential series, in the initial and intermediate stages shown FIGS. 12C and 12D, the spraying operation is in progress and not yet completed. In FIG. 12E, the spraying operation has been completed and most of the external surfaces of sensor 10 have been covered with one or more layers 33. Notwithstanding the foregoing, it should be understood that in other embodiments, the ink dispenser need not necessary move in a scanning motion, as will be discussed in greater detailer subsequently herein with for ink dispenser 37B with respect to FIGS. 13A-F.

Furthermore, while spraying is shown in figures, it should be understood that various techniques may be employed for forming and/or placing a layer 33 of light attenuating or blocking material. For example, the layer of light attenuating material may be formed and/or placed over the at least portions of the first and second external surfaces by one of spraying, dipping, brushing, rolling, electrodepositing, and/or sputtering the light attenuating material thereon.

Figure 12F:
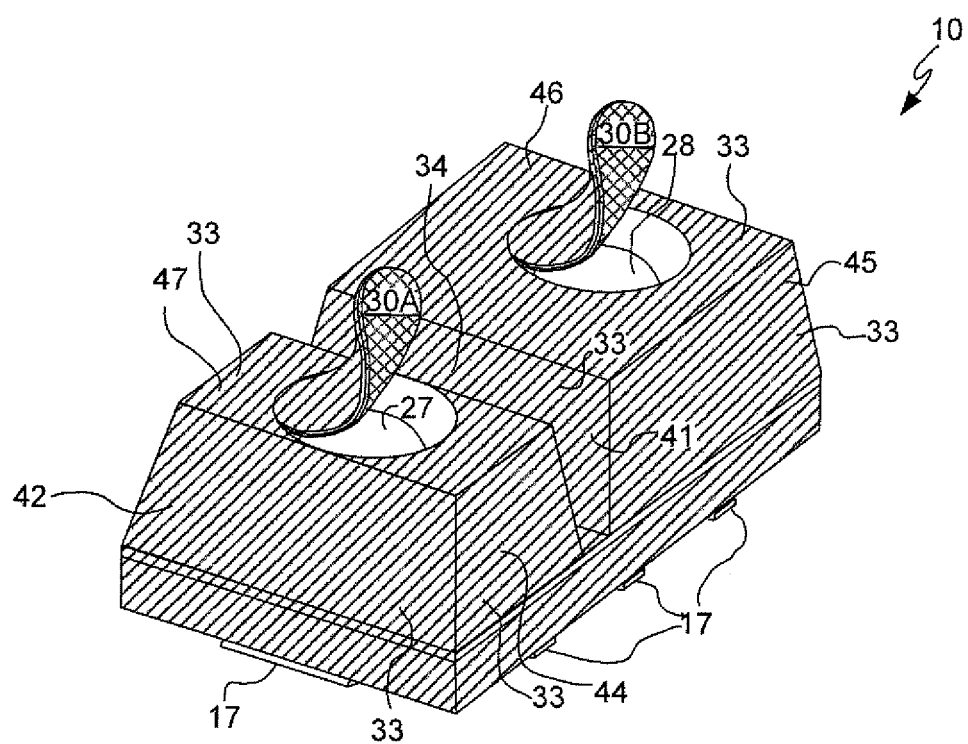
Figure 12G:
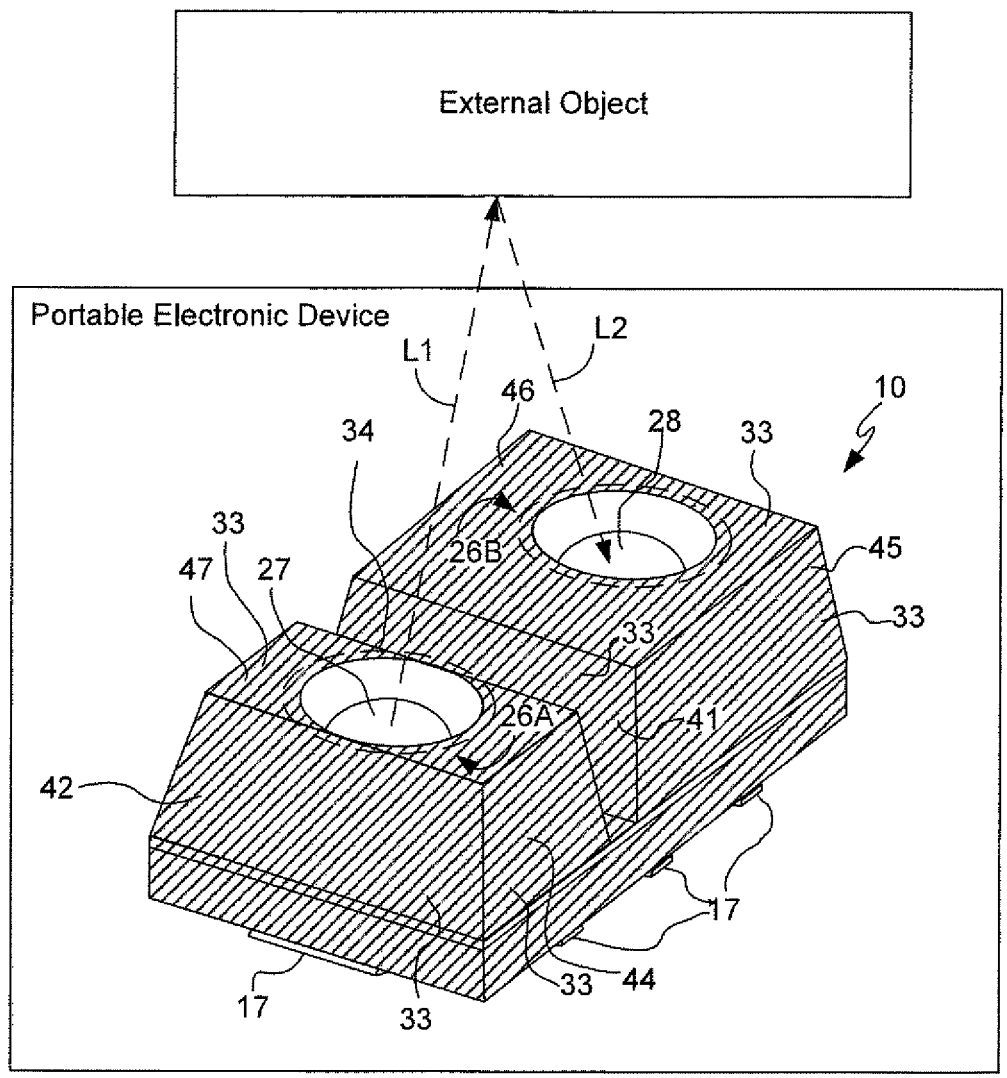
Figure 13A:
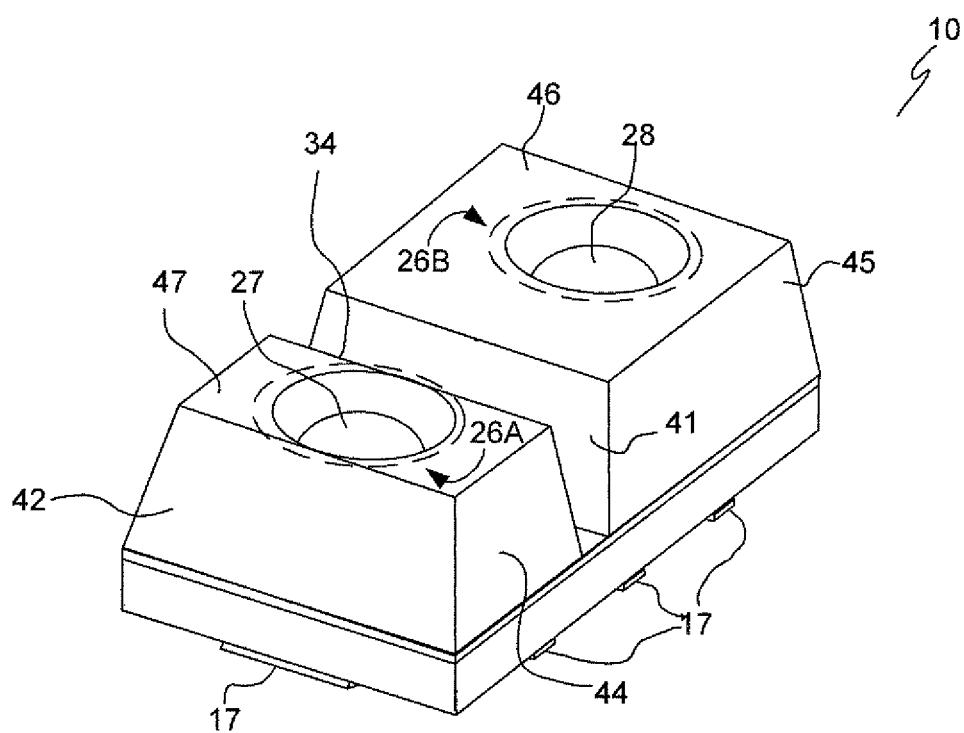
FIGS. 13A-13F are another sequential series of figures showing another embodiment of applying layers to external surfaces of a proximity sensor.
Figure 13B:
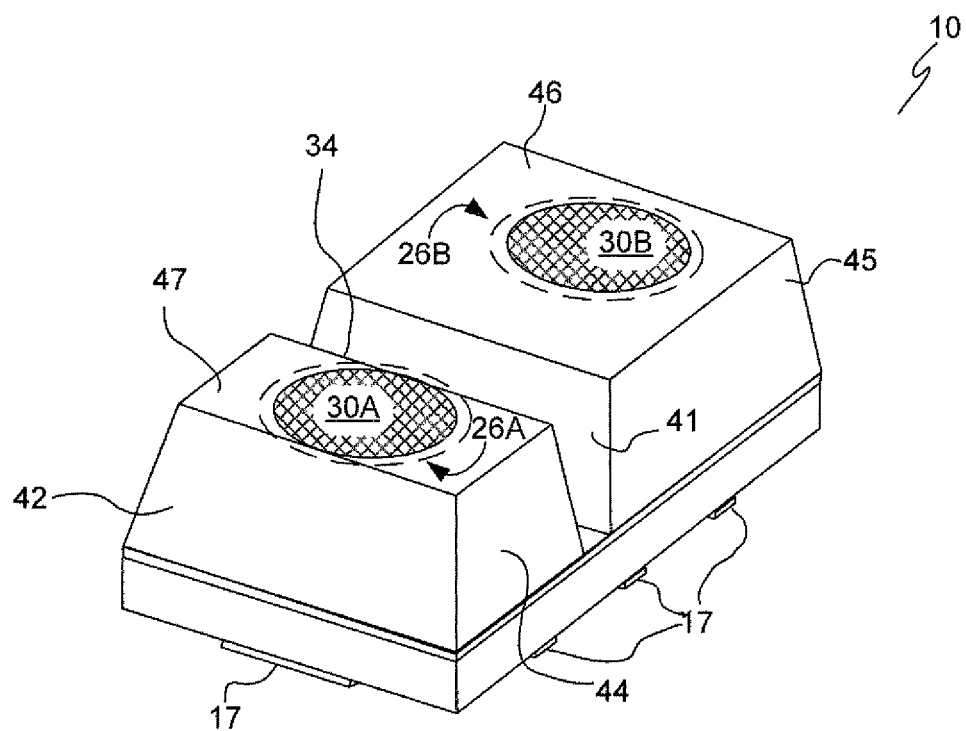
Figure 13C:
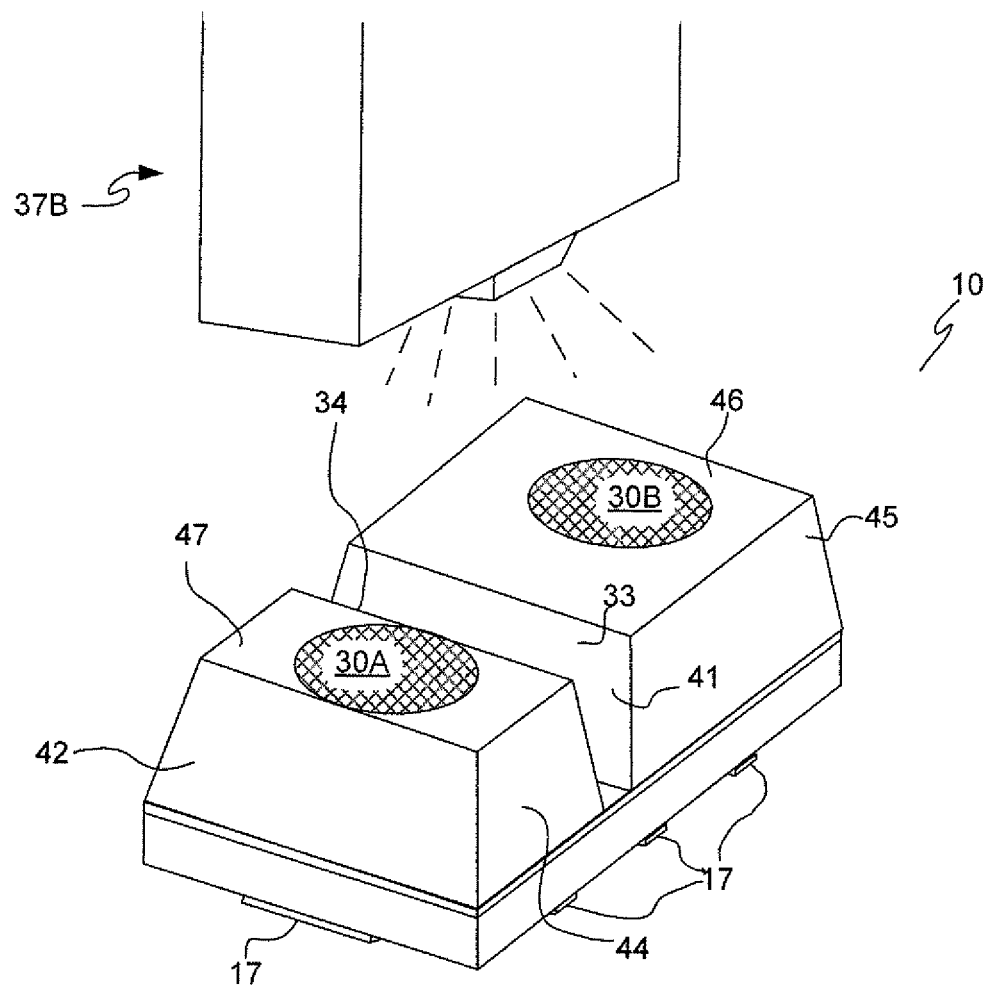
Figure 13D:
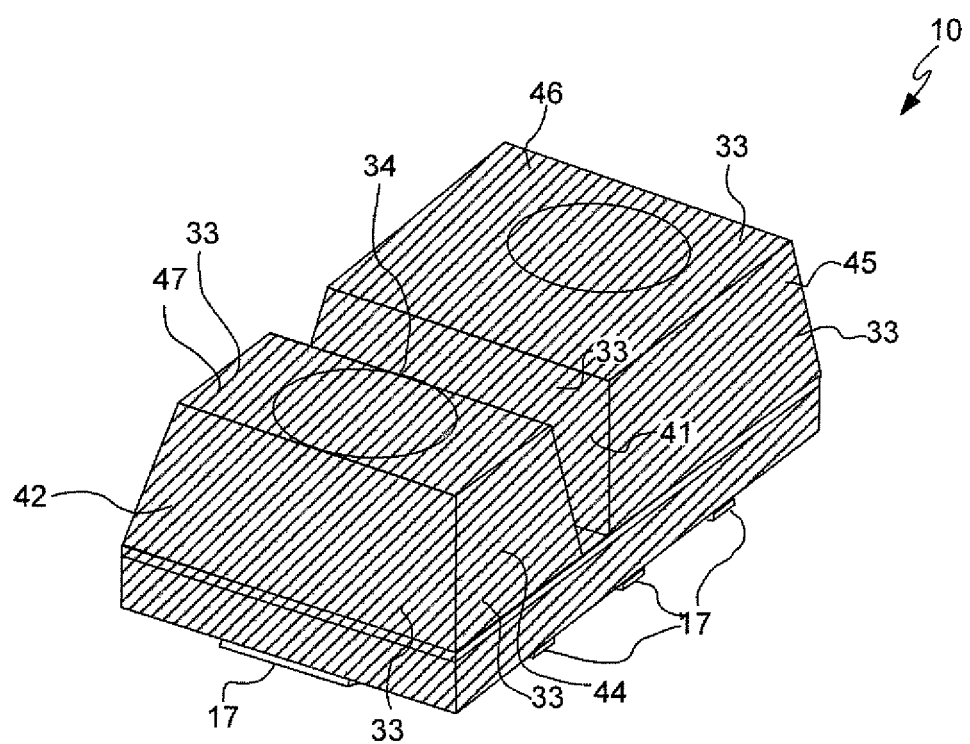
Figure 13E:
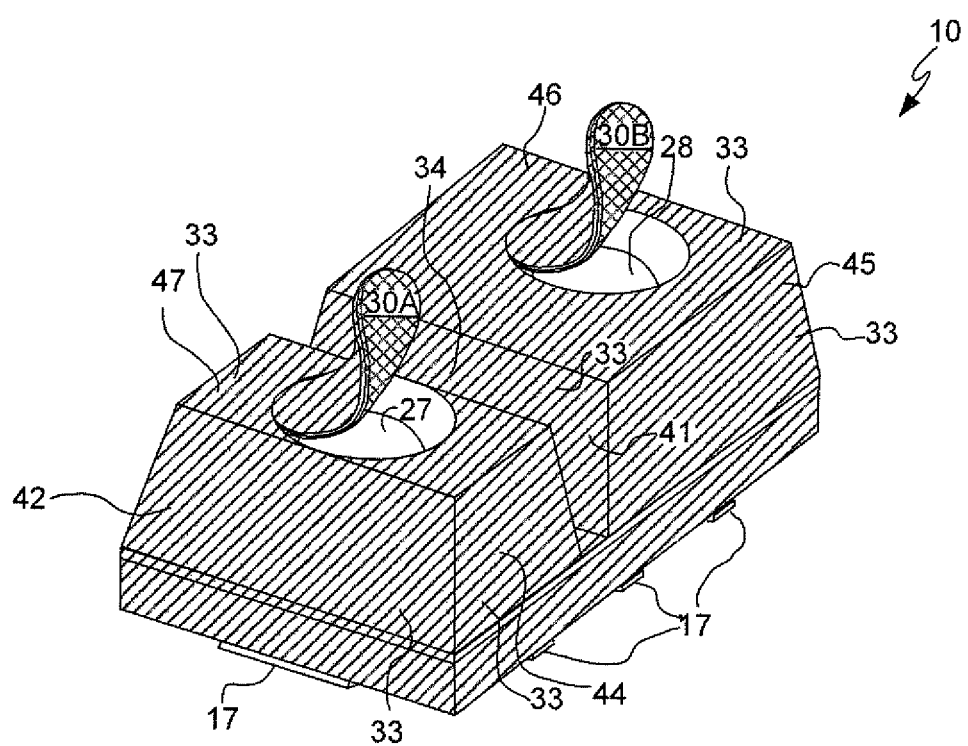
Figure 13F:
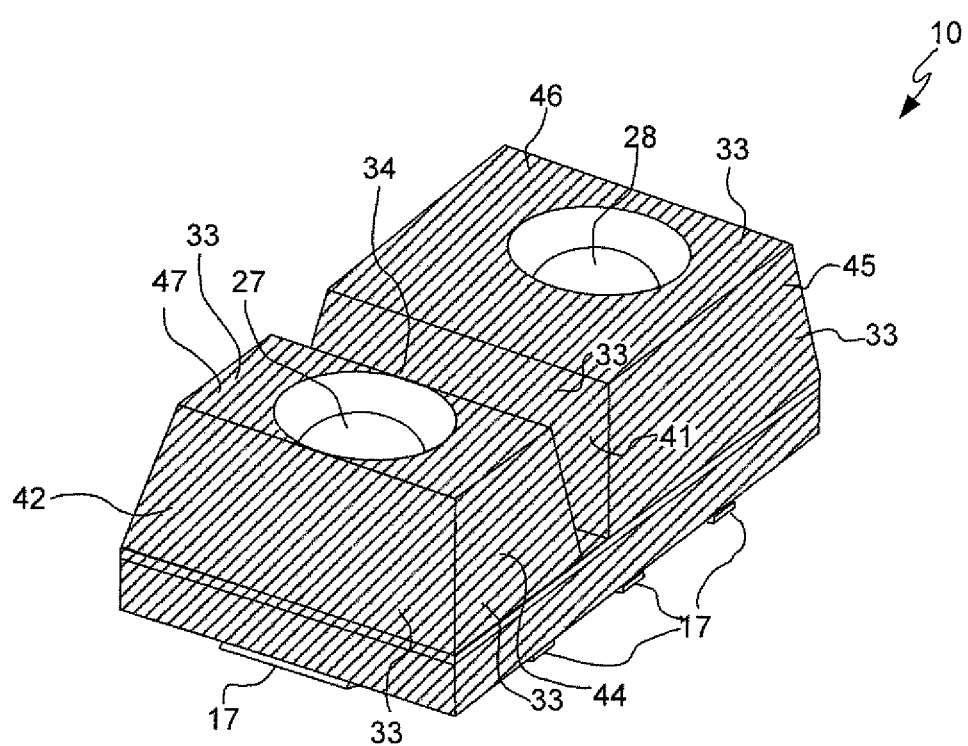

FIGS. 12F and 12G in sequential series show initial and final stages of removing the one or more removeable masking layers 30A, 30B from the first and second masking regions 26A, 26B of the first and second external surfaces 46, 47. Since the one or more removeable masking layers 30A, 30B may be sandwiched between at least a portion of the layer 33 of light attenuating material and the first and second masking regions 26A, 26B, it should be understood that the first and second lenses 27, 28 (and/or first and second masking regions 26A, 26B) may be shielded from the layer 33 of light attenuating material by the one or more layers of masking material 30A, 30B. Moreover, in light of the foregoing sandwiching, removal of the one or more removeable masking layers 30A, 30B as shown in FIGS. 12F and 12G may likewise remove a portion of the of the layer 33 of light attenuating material from over the first and second lenses 27, 28 (and/or from over first and second masking regions 26A, 26B).

As particularly shown in FIG. 12F, the one or more removeable masking layers 30A, 30B may be peelable. The removing may comprise peeling the removeable masking layer from the first and second masking regions 26A, 26B of the first and second external surfaces 46, 47. In some embodiments, a directed jet of compressed air may be used to facilitate the peeling.

While peeling is shown in FIG. 12F, it should be understood that various techniques may be employed for removing the one or more removeable masking layers 30A, 30B. The particular technique used may relate to properties of the removeable masking material employed for the layers 30A, 30B. For example, the removeable masking layer may be dissolvable in a solvent (e.g. water). In such case, the removing may comprise dissolving the removeable masking layer in the solvent (e.g. water).

The sensor 10 shown in FIG. 12G, may comprise a substrate upon which the light emitter and the light detector are operably mounted. First lens 27 may be integrally formed with first light pass component, which may be disposed over and covering at least portions of the light emitter. First light pass component may comprise first external surfaces 47. Second lens 28 may be integrally formed with second light pass component, which may be disposed over and covering at least portions of the light detector. Second light pass component may comprise second external surfaces.

In FIG. 12G, at least portions of the first and second light pass components may be separated by a gap 34. For the sensor 10, its light emitter may comprise a semiconductor emitter die having a major emitter surface, and its light detector may comprise a semiconductor detector die having a major detector surface. The gap 34 separating the first and second light pass components may comprise a groove extending inwardly past at least one of the major emitter surface and the major detector surface to a base extremity of the groove. The first and second light pass components may be separated at least partially by the groove having the base extremity disposed therebetween.

The substrate of the proximity sensor 10 may comprise a lead frame having electrical contacts 17, which may be used to provide electrical connections between proximity sensor 10 and external devices. In one embodiment, the substrate 10 may be a PCB. The lead frame may have a first portion of the lead frame where the semiconductor emitter die is mounted, and having portion a second portion of the lead frame where the semiconductor detector die is mounted. The groove of gap 34 may extend inwardly, past at least one of the first portion of the lead frame where the semiconductor emitter die is mounted and the second portion of the lead frame where the semiconductor detector die is mounted, to the base extremity of the groove.

The layer 33 of light attenuating and/or blocking material may be disposed over at least portions of the first and second external surfaces 46, 47 located adjacent to the groove. The layer 33 of light attenuating and/or blocking material may be configured to attenuate and/or block substantially the transmission of undesired direct, scattered or reflected light between the light emitter and the light detector and thereby may substantially avoiding optical crosstalk and/or interference between the light emitter and the light detector.

The sensor 10 may be configured such that at least a first portion L1 of light emitted by the light emitter may pass through a first masking region 26A of the first light pass component that has been shielded from the layer 33 of light attenuating and/or blocking material. The sensor 10 may be configured such that at least a second portion L2 of the first portion L1 of light reflected from an object of interest in proximity to the sensor, to be detected by the light detector, passes through a second masking region 26B of the second light pass component that has been shielded from the layer 33 of light attenuating and/or blocking material.

First and second lenses 27, 28 may be first and second molded optically transmissive lenses 27, 28 and may be formed over the light emitter and the light detector, respectively. The first and second molded optically transmissive lenses 27, 28 may be shielded from the layer 33 of light attenuating and/or blocking material. The optical sensor 10 may be incorporated into a portable electronic device.

FIGS. 13A-13F are another sequential series of figures showing another embodiment of applying layers to external surfaces of a proximity sensor. FIGS. 13A-13F are generally similar to FIGS. 12A-12G as just discussed, however in the sequential series FIGS. 13A-13F the ink dispenser 37B is substantially stationary, and does not move in a scanning motion. Aside from the foregoing distinction, the elements shown in FIGS. 13A-F and their teachings are substantially the same as what was just discussed in detail with respect to FIGS. 12A-12G.

Figure 14:
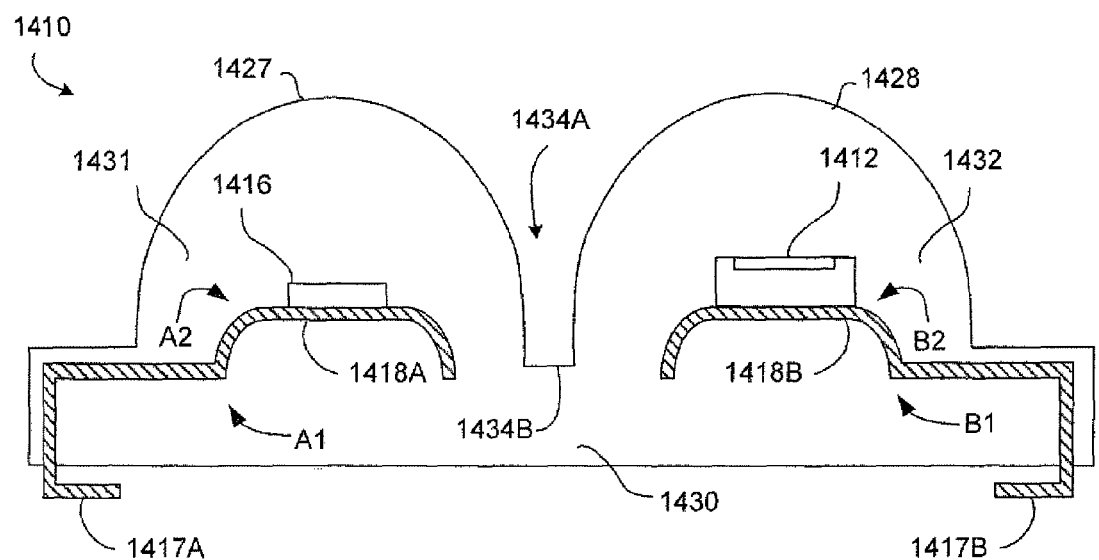
FIGS. 14-18 are cut away side views of additional embodiments.

FIG. 14 is a cut away side view of an additional embodiment. FIG. 14 shows an optical sensor 1410. The optical sensor 1410 may form at least a portion of a proximity sensor as discussed previously herein. The optical sensor 1410 may comprise a substrate. The substrate of the optical sensor may comprise a base portion 1430 molded over a lead frame.

Optical sensor 1410 may comprise a semiconductor light emitter die having a major emitter surface 1416, and a semiconductor light detector die having a major detector surface 1412. The semiconductor light emitter die may be mounted on a first portion 1418A of the lead frame. The semiconductor light detector die may be mounted on a second portion 1418B of the lead frame. Extremities 1417A, 1417B of the lead frame may provide electrical contacts 1417A, 1417B, which may be used to provide electrical connections between optical sensor 1410 and external devices.

As shown in FIG. 14, the lead frame may have a sequential pair of substantially equal opposing bends adjacent to one of the first and second portions of the lead frame 1418A, 1418B. For example, FIG. 14 shows a first sequential pair A1, A2 of substantially equal opposing bends adjacent the first portion 1418A of the lead frame, where the semiconductor light emitter die is mounted on the lead frame. For example, FIG. 14 further shows a second sequential pair B1, B2 of substantially equal opposing bends adjacent the second portion 1418B of the lead frame, where the semiconductor light detector die is mounted on the lead frame. The first and second sequential pairs A1, A2, B1, B2 of substantially equal opposing bends may be configured to raise the position of the semiconductor dies relative to the base portion 1430.

As shown in FIG. 14, a first light pass component 1431 may be disposed over and covering at least portions of the semiconductor light emitter die. The first light pass component 1431 may comprise first external surfaces thereof 1427. First external surface 1427 of the first light pass component 1431 may comprise a first optically transmissive lens 1427 having a substantially hemispherical dome shape.

Similarly, a second light pass component 1432 may be disposed over and covering at least portions of the semiconductor light detector die. The second light pass component 1432 may comprise second external surfaces thereof 1428. Second external surface 1428 of the second light pass component 1432 may comprise a second optically transmissive lens 1428, likewise having a substantially hemispherical dome shape. As discussed previously, the first and second sequential pairs A1, A2, B1, B2 of substantially equal opposing bends may be configured to raise the position of the semiconductor light emitter and receiver dies relative to the first and second light pass components 1431, 1432. As a result, the semiconductor light emitter and receiver dies may be arranged further from the base portion 1430, and thereby, may reduce crosstalk that may otherwise occur through the base portion 1430.

The first and second light pass components 1431, 1432 may be separated at least partially by a groove 1434A having a base extremity 1434B disposed therebetween. The groove 1434A may be formed by sawing. The groove 1434A may extend inwardly past at least one of the first and second portions 1418A, 1418B of the lead frame to the base extremity 1434B of the groove.

The groove 1434A may be configured to attenuate and/or block substantially the transmission of undesired direct, scattered or reflected light between the semiconductor light emitter die and the semiconductor light detector die and may thereby substantially avoid optical crosstalk and/or interference between the semiconductor light emitter die and the semiconductor light detector die. In particular, since crosstalk may otherwise occur via transmission through the base portion 1430 of the substrate, avoidance of crosstalk may be furthered by raising the emitter and detector dies through the first and second sequential pairs A1, A2, B1, B2 of substantially equal opposing bends and/or deepening groove 1434A.

Figure 15:
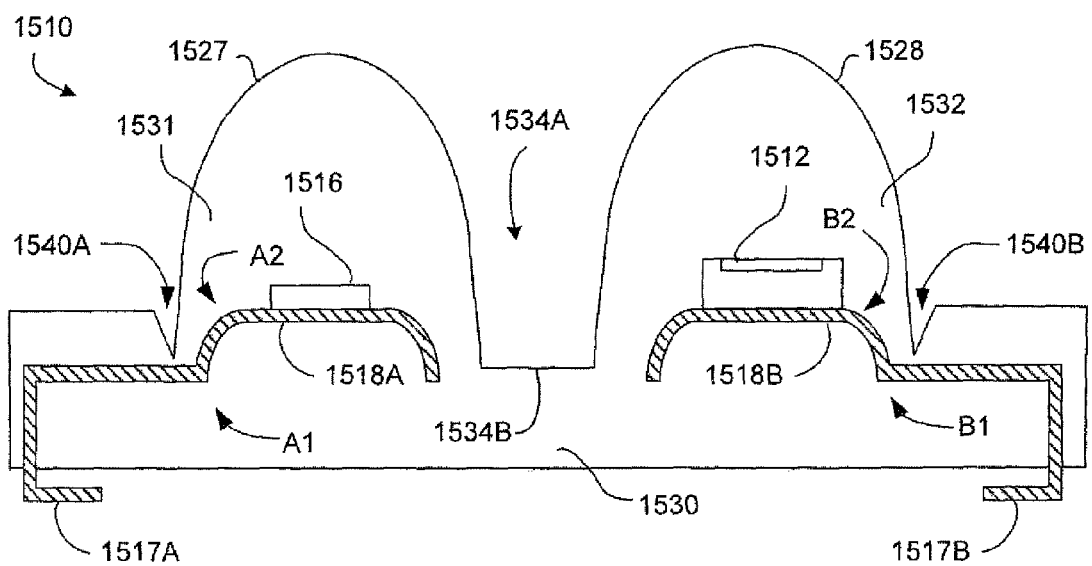

FIG. 15 is a cut away side view of an additional embodiment. FIG. 15 shows an optical sensor 1510. The optical sensor may form at least a portion of a proximity sensor as discussed previously herein.

Optical sensor 1510 may comprise a semiconductor light emitter die having a major emitter surface 1516, and a semiconductor light detector die having a major detector surface 1512. The semiconductor light emitter die may be mounted on a first portion 1518A of a lead frame. The semiconductor light detector die may be mounted on a second portion 1518B of the lead frame. Extremities 1517A, 1517B of the lead frame may provide electrical contacts 1517A, 1517B, which may be used to provide electrical connections between optical sensor 1510 and external devices.

The optical sensor 1510 may comprise a substrate. The substrate of the optical sensor 1510 may comprise a base portion 1530 molded over the first and second portions 1518A, 1518B of the lead frame.

As shown in FIG. 15, the lead frame may have a sequential pair of substantially equal opposing bends adjacent to one of the first and second portions of the lead frame 1518A, 1518B. For example, FIG. 15 shows a first sequential pair A1, A2 of substantially equal opposing bends adjacent the first portion 1518A of the lead frame, where the semiconductor light emitter die is mounted on the lead frame. For example, FIG. 15 further shows a second sequential pair B1, B2 of substantially equal opposing bends adjacent the second portion 1518B of the lead frame, where the semiconductor light detector die is mounted on the lead frame.

As shown in FIG. 15, a first light pass component 1531 may be disposed over and covering at least portions of the semiconductor light emitter die. The first light pass component may comprise first external surfaces thereof 1527. First external surface 1527 of the first light pass component 1531 may comprise a first optically transmissive lens 1527 having a substantially hemispherical dome shape. As shown in FIG. 15, the substantially hemispherical dome shape of the first optically transmissive lens 1527 may be substantially prolate.

Similarly, a second light pass component 1532 may be disposed over and covering at least portions of the semiconductor light detector die. The second light pass component 1532 may comprise second external surfaces thereof 1528. Second external surface 1528 of the second light pass component 1532 may comprise a second optically transmissive lens 1528, likewise having a substantially hemispherical dome shape. As shown in FIG. 15, the substantially hemispherical dome shape of the second optically transmissive lens 1528 may likewise be substantially prolate.

The first and second light pass components 1531, 1532 may be separated at least partially by a groove 1534A having a base extremity 1534B disposed therebetween. The groove 1534A may be formed by sawing. The groove 1534A may extend inwardly past at least one of the first and second portions 1518A, 1518B of the lead frame to the base extremity 1534B of the groove. The groove may be configured to attenuate and/or block substantially the transmission of undesired direct, scattered or reflected light between the semiconductor light emitter die and the semiconductor light detector die and may thereby substantially avoid optical crosstalk and/or interference between the semiconductor light emitter die and the semiconductor light detector die. Groove 1534A may extend around a base of first dome lens 1527 and around a base of second dome lens 1528, so as to provide additional perimeter indentations 1540A, 1540B. Additionally, the first and second portions 1518A, 1518B of the lead frame may be made larger covering bottom portion of the first and second second optically transmissive lens 1527, 1528 surrounded by the perimeter indentations 1540A, 1540B such that light falling on the first and second portions 1518A, 1518B may be substantially prevented from entering the base portion 1530. The foregoing may further avoidance of crosstalk.

Figure 16:
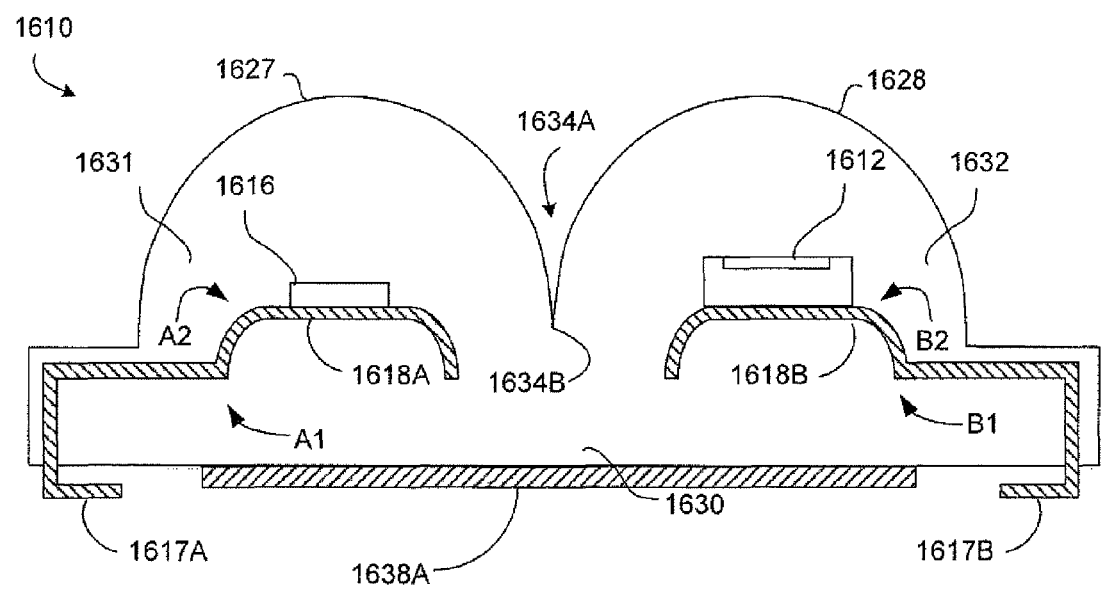

FIG. 16 is a cut away side view of an additional embodiment. FIG. 16 shows an optical sensor 1610. The optical sensor may form at least a portion of a proximity sensor as discussed previously herein.

Optical sensor 1610 may comprise a semiconductor light emitter die having a major emitter surface 1616, and a semiconductor light detector die having a major detector surface 1612. The semiconductor light emitter die may be mounted on a first portion 1618A of a lead frame. The semiconductor light detector die may be mounted on a second portion 1618B of the lead frame. Extremities 1617A, 1617B of the lead frame may provide electrical contacts 1617A, 1617B, which may be used to provide electrical connections between optical sensor 1610 and external devices.

The optical sensor 1610 may comprise a substrate. The substrate of the optical sensor 1610 may comprise a base portion 1630 molded over the first and second portions 1618A, 1618B of the lead frame. The substrate may further comprise a third portion 1638A of the lead frame arranged proximate to a side of the optical sensor opposing the groove 1634A and the base extremity 1634B of the groove. The molded base portion 1630 may be sandwiched between the third portion 1638A of the lead frame and the groove 1634A. As shown in FIG. 16, in some embodiments the base exteremity 1634B of the groove may not be flat.

As shown in FIG. 16, the lead frame may have a sequential pair of substantially equal opposing bends adjacent to one of the first and second portions of the lead frame 1618A, 1618B. For example, FIG. 16 shows a first sequential pair A1, A2 of substantially equal opposing bends adjacent the first portion 1618A of the lead frame, where the semiconductor light emitter die is mounted on the lead frame. For example, FIG. 16 further shows a second sequential pair B1, B2 of substantially equal opposing bends adjacent the second portion 1618B of the lead frame, where the semiconductor light detector die is mounted on the lead frame.

As shown in FIG. 16, a first light pass component 1631 may be disposed over and covering at least portions of the semiconductor light emitter die. The first light pass component may comprise first external surfaces thereof 1627. First external surface 1627 of the first light pass component 1631 may comprise a first optically transmissive lens 1627 having a substantially hemispherical dome shape.

Similarly, a second light pass component 1632 may be disposed over and covering at least portions of the semiconductor light detector die. The second light pass component 1632 may comprise second external surfaces thereof 1628. Second external surface 1628 of the second light pass component 1632 may comprise a second optically transmissive lens 1628, likewise having a substantially hemispherical dome shape.

The first and second light pass components 1631, 1632 may be separated at least partially by a groove 1634A having a base extremity 1634B disposed therebetween. The groove 1634A may be formed by pre-molding the first and second light pass components 1631, 1632 and followed by adjoining thereby the first and second light pass components 1631, 1632 to form a pointing base extremity 1634B as shown in FIG. 16. The groove 1634A may extend inwardly past at least one of the first and second portions 1618A, 1618B of the lead frame to the base extremity 1634B of the groove. The groove 1634A may extend deeper and/or lower relative to first and second lead frame 1618A, 1618B and therefore may be configured to attenuate and/or block substantially the transmission of undesired direct, scattered or reflected light between the semiconductor light emitter die and the semiconductor light detector die and may thereby substantially avoid optical crosstalk and/or interference between the semiconductor light emitter die and the semiconductor light detector die. As the groove 1634A extends further past at least one of the first and second portions 1618A, 1618B, further structural reinforcement of the molded base portion 1630 may be desirable. As shown in FIG. 16, the third portion 1638A of the lead frame may provide structural reinforcement of the molded base portion 1630. The third portion 1638A of the lead frame may each extend from proximate to the first portion 1618A of the lead frame, past the base extremity 1634B of the groove 1634A, to proximate to second portion 1618B of the lead frame.

Figure 17:
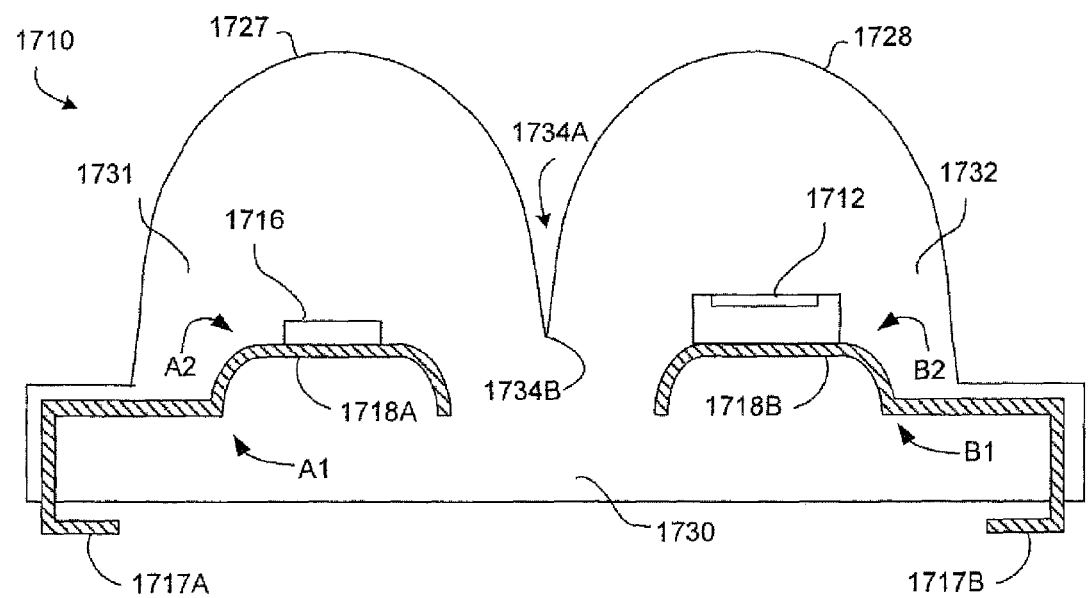

FIG. 17 is a cut away side view of an additional embodiment. FIG. 17 shows an optical sensor 1710. The optical sensor may form at least a portion of a proximity sensor as discussed previously herein.

Optical sensor 1710 may comprise a semiconductor light emitter die having a major emitter surface 1716, and a semiconductor light detector die having a major detector surface 1712. The semiconductor light emitter die may be mounted on a first portion 1718A of a lead frame. The semiconductor light detector die may be mounted on a second portion 1718B of the lead frame. Extremities 1717A, 1717B of the lead frame may provide electrical contacts 1717A, 1717B, which may be used to provide electrical connections between optical sensor 1710 and external devices.

The optical sensor 1710 may comprise a substrate. The substrate of the optical sensor 1710 may comprise a base portion 1730 molded over the first and second portions 1718A, 1718B of the lead frame.

As shown in FIG. 17, the lead frame may have a sequential pair of substantially equal opposing bends adjacent to one of the first and second portions of the lead frame 1718A, 1718B. For example, FIG. 17 shows a first sequential pair A1, A2 of substantially equal opposing bends adjacent the first portion 1718A of the lead frame, where the semiconductor light emitter die is mounted on the lead frame. For example, FIG. 17 further shows a second sequential pair B1, B2 of substantially equal opposing bends adjacent the second portion 1718B of the lead frame, where the semiconductor light detector die is mounted on the lead frame.

As shown in FIG. 17, a first light pass component 1731 may be disposed over and covering at least portions of the semiconductor light emitter die. The first light pass component may comprise first external surfaces thereof 1727. First external surface 1727 of the first light pass component 1731 may comprise a first optically transmissive lens 1727 having a substantially hemispherical dome shape. As shown in FIG. 17, the substantially hemispherical dome shape of the first optically transmissive lens 1727 may be substantially prolate.

Similarly, a second light pass component 1732 may be disposed over and covering at least portions of the semiconductor light detector die. The second light pass component 1732 may comprise second external surfaces thereof 1728. Second external surface 1728 of the second light pass component 1732 may comprise a second optically transmissive lens 1728, likewise having a substantially hemispherical dome shape. As shown in FIG. 17, the substantially hemispherical dome shape of the second optically transmissive lens 1728 may be substantially prolate. By raising the position of the semiconductor light emitter and detector dies, the distance between the dies and external surfaces of the first and second lenses 1727, 1728 may present design challenges for efficiency of operation of the lenses. This may be overcome by having the substantially prolate shape.

The first and second light pass components 1731, 1732 may be separated at least partially by a groove 1734A having a base extremity 1734B disposed therebetween. The groove 1734A may extend inwardly past at least one of the major emitter surface 1716 and the major detector surface 1712 to the base extremity 1734B of the groove. The groove may be configured to attenuate and/or block substantially the transmission of undesired direct, scattered or reflected light between the semiconductor light emitter die and the semiconductor light detector die and may thereby substantially avoid optical crosstalk and/or interference between the semiconductor light emitter die and the semiconductor light detector die.

Figure 18:
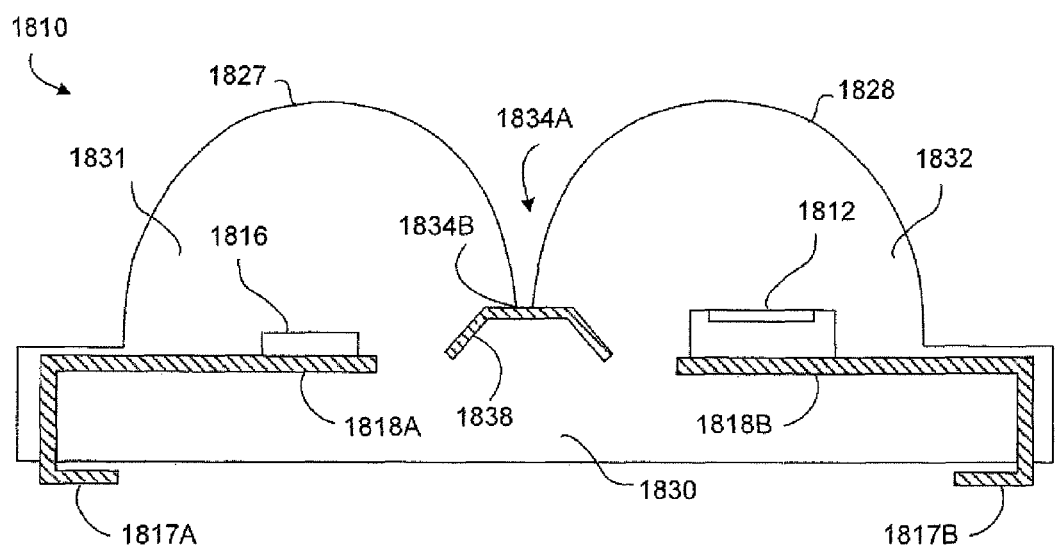

FIG. 18 is a cut away side view of an additional embodiment. FIG. 18 shows an optical sensor 1810. The optical sensor may form at least a portion of a proximity sensor as discussed previously herein.

Optical sensor 1810 may comprise a semiconductor light emitter die having a major emitter surface 1816, and a semiconductor light detector die having a major detector surface 1812. The semiconductor light emitter die may be mounted on a first portion 1818A of a lead frame. The semiconductor light detector die may be mounted on a second portion 1818B of the lead frame. Extremities 1817A, 1817B of the lead frame may provide electrical contacts 1817A, 1817B, which may be used to provide electrical connections between optical sensor 1810 and external devices.

As shown in FIG. 18, a first light pass component 1831 may be disposed over and covering at least portions of the semiconductor light emitter die. The first light pass component may comprise first external surfaces thereof 1827. First external surface 1827 of the first light pass component 1831 may comprise a first optically transmissive lens 1827 having a substantially hemispherical dome shape.

Similarly, a second light pass component 1832 may be disposed over and covering at least portions of the semiconductor light detector die. The second light pass component 1832 may comprise second external surfaces thereof 1828. Second external surface 1828 of the second light pass component 1832 may comprise a second optically transmissive lens 1828, likewise having a substantially hemispherical dome shape. The first and second light pass components 1831, 1832 may be separated at least partially by a groove 1834A having a base extremity 1834B disposed therebetween.

The optical sensor 1810 may comprise a substrate. The substrate of the optical sensor 1810 may comprise a base portion 1830 molded over the first and second portions 1818A, 1818B of the lead frame. A third portion 1838 of the lead frame may be interposed between the dies, more specifically, between the major emitter surface 1816 and the major detector surface 1812. The third portion 1838 of the lead frame may be bent to define a reflective portion for directing light falling thereon back to the respective first and second light pass components 1831, 1832. Thus, the third portion 1838 of the lead frame may be configured to attenuate and/or block substantially the transmission of undesired direct, scattered and/or reflected light between the major emitter surface 1816 and the major detector surface 1812 and may thereby substantially avoid optical crosstalk and interference between the major emitter surface 1816 and the major detector surface 1812

Figure 19A:
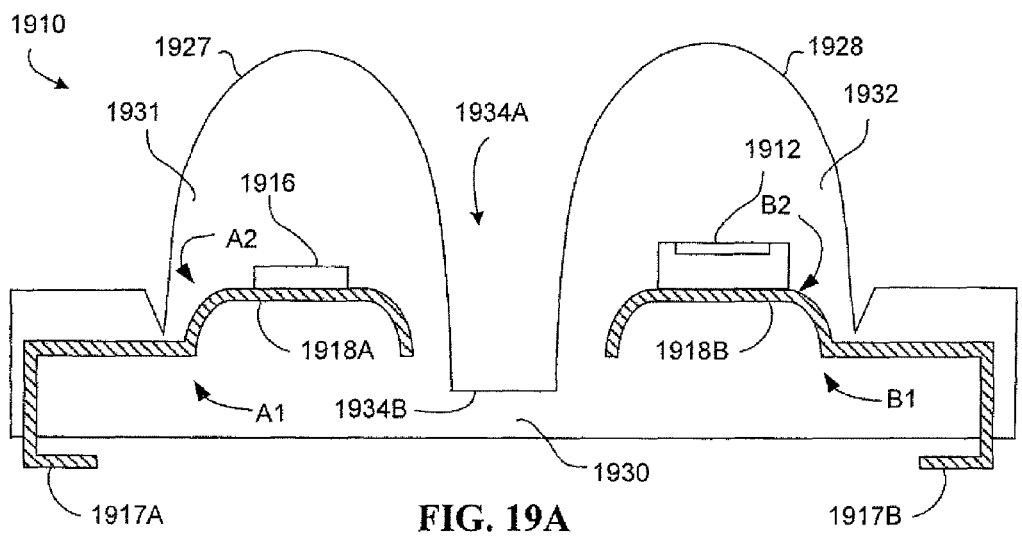
FIGS. 19A and 19B are a cut away side view and a cut away top view of another additional embodiment.
Figure 19B:
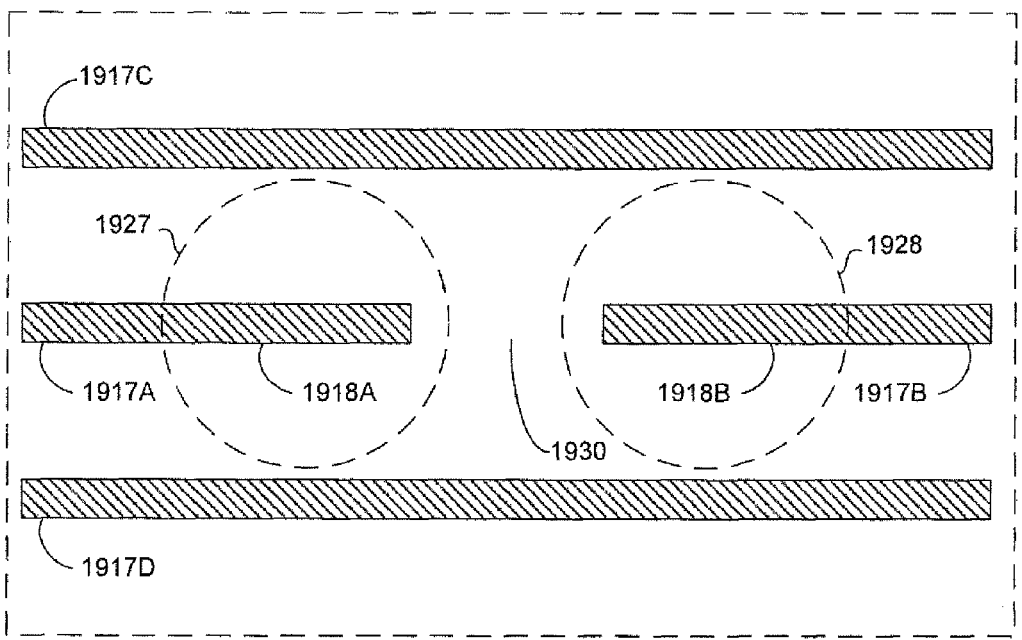

FIGS. 19A and 19B are a cut away side view and a cut away top view, respectively, of another additional embodiment. FIGS. 19A and 19B show an optical sensor 1910. The optical sensor may form at least a portion of a proximity sensor as discussed previously herein.

Optical sensor 1910 may comprise a semiconductor light emitter die having a major emitter surface 1916, and a semiconductor light detector die having a major detector surface 1912. The semiconductor light emitter die may be mounted on a first portion 1918A of a lead frame. The semiconductor light detector die may be mounted on a second portion 1918B of the lead frame. Extremities 1917A, 1917B of the lead frame may provide electrical contacts 1917A, 1917B, which may be used to provide electrical connections between optical sensor 1910 and external devices.

The optical sensor 1910 may comprise a substrate. The substrate of the optical sensor 1910 may comprise a base portion 1930 molded over the first and second portions 1918A, 1918B of the lead frame.

As particularly shown in FIG. 19A, the lead frame may have a sequential pair of substantially equal opposing bends adjacent to one of the first and second portions of the lead frame 1918A, 1918B. For example, FIG. 19A shows a first sequential pair A1, A2 of substantially equal opposing bends adjacent the first portion 1918A of the lead frame, where the semiconductor light emitter die is mounted on the lead frame. For example, FIG. 19A further shows a second sequential pair B1, B2 of substantially equal opposing bends adjacent the second portion 1918B of the lead frame, where the semiconductor light detector die is mounted on the lead frame.

As shown in FIG. 19A, a first light pass component 1931 may be disposed over and covering at least portions of the semiconductor light emitter die. The first light pass component may comprise first external surfaces thereof 1927. First external surface 1927 of the first light pass component 1931 may comprise a first optically transmissive lens 1927 having a substantially hemispherical dome shape. As shown in FIG. 19A, the substantially hemispherical dome shape of the first optically transmissive lens 1927 may be substantially prolate.

Similarly, a second light pass component 1932 may be disposed over and covering at least portions of the semiconductor light detector die. The second light pass component 1932 may comprise second external surfaces thereof 1928. Second external surface 1928 of the second light pass component 1932 may comprise a second optically transmissive lens 1928, likewise having a substantially hemispherical dome shape. As shown in FIG. 19A, the substantially hemispherical dome shape of the second optically transmissive lens 1928 may likewise be substantially prolate.

The first and second light pass components 1931, 1932 may be separated at least partially by a groove 1934A having a base extremity 1934B disposed therebetween. The groove 1934A may extend inwardly past at least one of the first and second portions 1918A, 1918B of the lead frame to the base extremity 1934B of the groove. The groove may be configured to attenuate and/or block substantially the transmission of undesired direct, scattered or reflected light between the semiconductor light emitter die and the semiconductor light detector die and may thereby substantially avoid optical crosstalk and/or interference between the semiconductor light emitter die and the semiconductor light detector die.

As the groove 1934A extends further past at least one of the first and second portions 1918A, 1918B, further structural reinforcement of the molded base portion 1930 may be desirable. As shown in cut away top view in FIG. 19B, third and fourth portions 1917C, 1917D of the lead frame may provide structural reinforcement of the molded base portion 1930. The third and fourth portions 1917C, 1917D of the lead frame may each extend from proximate to the first portion 1918A of the lead frame, past the base extremity 1934B of the groove 1934A, to proximate to second portion 1918B of the lead frame. The third and fourth portions 1917C, 1917D of the lead frame may arranged proximate to a perimeter and/or peripheral of optical sensor 1910, which may provide structural reinforcement of the molded base portion 1930, while substantially avoiding presence of the third and fourth portions 1917C, 1917D of the lead frame proximate to a central area of the molded base portion 1930.

Figure 20:
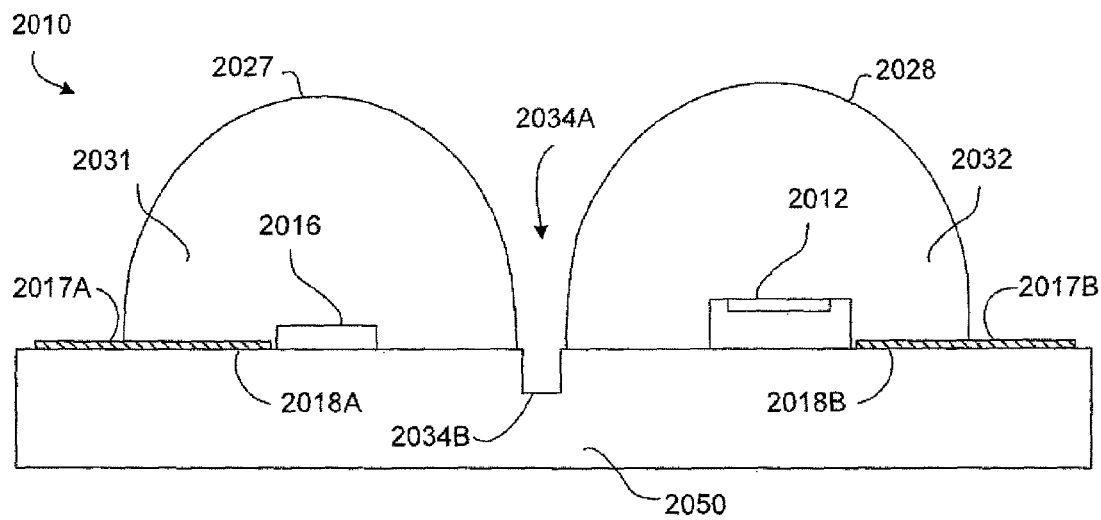
FIG. 20 is a cut away side view of yet another additional embodiment.

FIG. 20 is a cut away side view of yet another additional embodiment. FIG. 20 shows an optical sensor 2010. The optical sensor may form at least a portion of a proximity sensor as discussed previously herein.

The optical sensor 2010 may comprise a substrate. The substrate of the optical sensor 2010 may comprise a printed circuit board 2050 having one or more circuit leads comprising a lead frame disposed thereon. Optical sensor 2010 may comprise a semiconductor light emitter die having a major emitter surface 2016, and a semiconductor light detector die having a major detector surface 2012. The semiconductor light emitter die may be mounted on a first portion 2018A one of the circuit leads. The semiconductor light detector die may be mounted on a second portion 2018B of another one of the circuit leads. Extremities 2017A, 2017B of the leads may provide electrical contacts 2017A, 2017B, which may be used to provide electrical connections between optical sensor 2010 and external devices.

As shown in FIG. 20, a first light pass component 2031 may be disposed over and covering at least portions of the semiconductor light emitter die. The first light pass component may comprise first external surfaces thereof 2027. First external surface 2027 of the first light pass component 2031 may comprise a first optically transmissive lens 2027 having a substantially hemispherical dome shape.

Similarly, a second light pass component 2032 may be disposed over and covering at least portions of the semiconductor light detector die. The second light pass component 2032 may comprise second external surfaces thereof 2028. Second external surface 2028 of the second light pass component 2032 may comprise a second optically transmissive lens 2028, likewise having a substantially hemispherical dome shape. The first and second light pass components 2031, 2032 may be premolded and attached to substrate 2050 through an epoxy. On some occasions, the epoxy may optically couple the first light pass components 2031 to the second light pass components 2032, providing an unwanted optical bridge.

The first and second light pass components 2031, 2032 may be separated at least partially by a groove 2034A having a base extremity 2034B disposed therebetween. The groove 2034A may extend inwardly past at least one of the first and second portions 2018A, 2018B of the leads to the base extremity 2034B of the groove. The base extremity 2034B of the groove may extend into the printed circuit board 2050, substantially eliminating possibilities of having an unwanted optical bridge therebetween. The groove may be configured to attenuate and/or block substantially the transmission of undesired direct, scattered or reflected light between the semiconductor light emitter die and the semiconductor light detector die and may thereby substantially avoid optical crosstalk and/or interference between the semiconductor light emitter die and the semiconductor light detector die.

Figure 21:
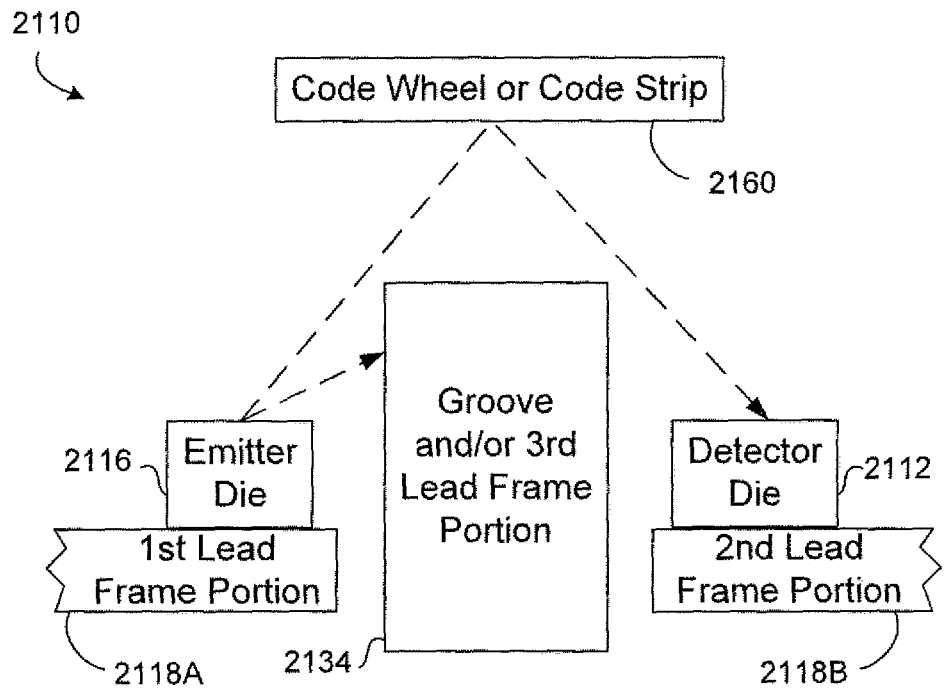
FIG. 21 is a block diagram of a reflective encoder according to another embodiment.

FIG. 21 is a block diagram of a reflective encoder 2110 according to another embodiment. Reflective encoder 2110 may comprise a semiconductor light emitter die 2116, and a semiconductor light detector die 2112. A first portion of light may be emitted by the light emitter die 2116 to code wheel or code strip 2160. The reflective encoder 2110 may be configured such that at least a second portion of the first portion of light may be reflected from code wheel or code strip 2160, to be detected by the semiconductor light detector die 2160.

The semiconductor light emitter die 2116 may be mounted on a first portion 2118A of a lead frame. The semiconductor light detector die 2112 may be mounted on a second portion 2118B of the lead frame. A groove 2134A and/or a third lead frame portion may be arranged to separate, at least partially, first and second light pass components (not shown). The groove 2134A and/or third lead frame portion may extend past at least one of the first and second portions 2118A, 2118B of the lead frame. The groove 2134A and/or third lead frame portion may be configured to attenuate and/or block substantially the transmission of undesired direct, scattered or reflected light between the semiconductor light emitter die and the semiconductor light detector die and may thereby substantially avoid optical crosstalk and/or interference between the semiconductor light emitter die 2116 and the semiconductor light detector die 2112.

Figure 22:
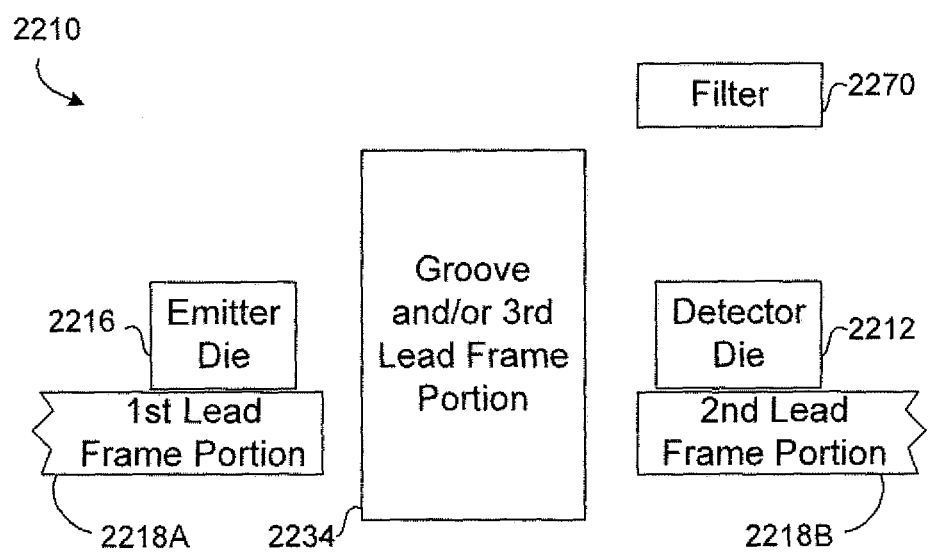
FIG. 22 is a block diagram of a color sensor according to another embodiment.

FIG. 22 is a block diagram of a color sensor according to another embodiment. Color sensor 2210 may comprise a semiconductor light emitter die 2116, and a semiconductor light detector die 2112. A first portion of light may be emitted by the light emitter die 2116 an external colored object. The color sensor 2210 may be configured such that at least a second portion of the first portion of light may be reflected from the external colored object, to be detected by the semiconductor light detector die 2160 through color filter 2270.

The semiconductor light emitter die 2116 may be mounted on a first portion 2118A of a lead frame. The semiconductor light detector die 2112 may be mounted on a second portion 2118B of the lead frame. A groove 2134A and/or a third lead frame portion may be arranged to separate, at least partially, first and second light pass components (not shown). The groove 2134A and/or third lead frame portion may extend past at least one of the first and second portions 2118A, 2118B of the lead frame. The groove 2134A and/or third lead frame portion may be configured to attenuate and/or block substantially the transmission of undesired direct, scattered or reflected light between the semiconductor light emitter die and the semiconductor light detector die and may thereby substantially avoid optical crosstalk and/or interference between the semiconductor light emitter die 2116 and the semiconductor light detector die 2112.

Included within the scope of the present invention are methods of making and having made the various components, devices and systems described herein.

Different aspects, embodiments or implementations may, either individually and/or in combination, but need not, yield one or more of the following advantages. For example, features such as raising the position of semiconductor dies by way of having sequential pairs A1, A2, B1, B2 of substantially equal opposing bends, the prolate lens, the portions of lead frame interposed between the semiconductor light emitter and detector dies, covering the light sensor with light attenuating or blocking layers may reduce crosstalk. Although different aspects have been presented in each embodiment, all or part of the different aspects illustrated in each embodiment may be combined. For example, the light attenuating or blocking layers may be applied to the embodiments shown in FIGS. 14-22.

Various embodiments of the invention are contemplated in addition to those disclosed hereinabove. The above-described embodiments should be considered as examples of the present invention, rather than as limiting the scope of the invention. In addition to the foregoing embodiments of the invention, review of the detailed description and accompanying drawings will show that there are other embodiments of the invention. Accordingly, many combinations, permutations, variations and modifications of the foregoing embodiments of the invention not set forth explicitly herein will nevertheless fall within the scope of the invention.

What is claimed is:

1. A method of making an optical sensor, comprising:
mounting a light emitter on a substrate, the light emitter comprising a semiconductor emitter die having a major emitter surface;
mounting a light detector on the substrate, the light detector being spaced apart from the light emitter on the substrate, the light detector comprising a semiconductor detector die having a major detector surface;
forming or placing a first light pass component over at least portions of the light emitter, the first light pass component comprising first external surfaces;
forming or placing a second light pass component over at least portions of the light detector such that at least portions of the first and second components are separated by a gap, the second light pass component comprising second external surfaces, the gap corresponding to a void of material, the gap formed by extending a groove inwardly past at least one of the major emitter surface and the major detector surface to a base extremity of the groove;
forming or placing a removeable masking layer over first and second masking regions of the first and second external surfaces;
forming or placing a layer of light attenuating or blocking material over at least portions of the first and second external surfaces located adjacent to the gap, the light attenuating material being configured to attenuate or block substantially transmission of undesired direct, scattered or reflected light between the light emitter and the light detector and thereby substantially avoid optical crosstalk and interference between the light emitter and the light detector; and
removing the removeable masking layer from the first and second masking regions of the first and second external surfaces.

2. The method of claim 1, wherein the layer of light attenuating material is one of a paint, an ink and a dye.

3. The method of claim 1, further comprising forming or placing at least a portion of the light attenuating material over the removeable masking layer, so that the removeable masking layer is sandwiched between at least a portion of the light attenuating material and the first and second masking regions.

4. The method of claim 1 further comprising curing the masking layer.

5. The method of claim 1 wherein:
the removeable masking layer is peelable; and
the removing comprising peeling the removeable masking layer from the first and second masking regions of the first and second external surfaces.

6. The method of claim 1 wherein:
the removeable masking layer is dissolvable in a solvent; and
the removing comprising dissolving the removeable masking layer.

7. The method of claim 1, further comprising forming or placing the light attenuating material over substantially most of the first and second external surfaces.

8. The method of claim 1, wherein the layer of light attenuating material is formed or placed over the at least portions of the first and second external surfaces by one of spraying, dipping, brushing, rolling, electrodepositing, and sputtering the light attenuating material thereon.

9. The method of claim 1, wherein the optical sensor is incorporated into a portable electronic device.

10. An optical sensor comprising:
a light emitter comprising a semiconductor emitter die having a major emitter surface;
a light detector comprising a semiconductor detector die having a major detector surface;
a first component disposed over and covering at least portions of the light emitter and comprising first external surfaces thereof, and a second component disposed over and covering at least portions of the light detector and comprising second external surfaces thereof, the first and second components being separated at least partially by a groove gap having a base extremity disposed therebetween, the groove corresponding to a void of material between the first component and second component, the groove formed by extending the groove inwardly past at least one of the major emitter surface and the major detector surface to a base extremity of the groove; and
a layer of light attenuating or blocking material disposed over at least portions of the first and second external surfaces located adjacent to the groove, and the light attenuating or blocking material is configured to attenuate or block substantially transmission of undesired direct, scattered or reflected light between the light emitter and the light detector and thereby substantially avoiding optical crosstalk and interference between the light emitter and the light detector,
wherein the sensor is configured such that at least a first portion of light emitted by the light emitter passes through a first region of the first component that has been shielded from the light attenuating or blocking material, and
wherein the sensor is configured such that at least a second portion of the first portion of light reflected from an object of interest in proximity to the sensor, to be detected by the light detector, passes through a second region of the second component that has been shielded from the light attenuating or blocking material.

11. The optical sensor of claim 10 wherein:
a molded optically transmissive lens is formed over the light emitter or the light detector; and
the molded optically transmissive lens has been shielded from the light attenuating or blocking material.

12. The optical sensor of claim 10, further comprising a substrate upon which the light emitter and the light detector are operably mounted.

13. The optical sensor of claim 10, wherein the optical sensor is incorporated into a portable electronic device.

14. The optical sensor of claim 10 wherein:
the optical sensor further comprises a lead frame having a first portion of the lead frame where the semiconductor emitter die is mounted, and having a second portion of the lead frame where the semiconductor detector die is mounted; and
the groove extends inwardly, past at least one of the first portion of the lead frame where the semiconductor emitter die is mounted and the second portion of the lead frame where the semiconductor detector die is mounted, to the base extremity of the groove.

15. An optical sensor comprising:
a lead frame;
a semiconductor light emitter die mounted on a first portion of the lead frame, the semiconductor light emitter die having a major emitter surface;

a semiconductor light detector die mounted on a second portion of the lead frame, the semiconductor light detector die having a major detector surface;

a first component disposed over and covering at least portions of the semiconductor light emitter die and comprising first external surfaces thereof; and a second component disposed over and covering at least portions of the semiconductor light detector die and comprising second external surfaces thereof, the first and second components being separated at least partially by a groove having a base extremity disposed therebetween, the groove corresponding to a void of material, wherein the groove extends inwardly past at least one of the major emitter surface and the major detector surface to the base extremity of the groove, and wherein the groove is configured to attenuate or block substantially transmission of undesired direct, scattered or reflected light between the semiconductor light emitter die and the semiconductor light detector die and thereby substantially avoid optical crosstalk and interference between the semiconductor light emitter die and the semiconductor light detector die.

16. The optical sensor as recited in claim 15 wherein the first and second components comprise first and second optically transmissive lenses each having a substantially hemispherical dome shape.

17. The optical sensor as recited in claim 16 wherein the substantially hemispherical dome shape is substantially prolate.

18. The optical sensor as recited in claim 15 wherein the optical sensor forms at least a portion of one of a proximity sensor, a reflective encoder and a color sensor.

19. The optical sensor as recited in claim 15 further comprising a sequential pair of substantially complementary opposing bends in the lead frame adjacent to one of the first and second portions of the lead frame.

20. An optical sensor comprising:

a semiconductor light emitter die having a major emitter surface;

a semiconductor light detector die having a major detector surface; and a lead frame, wherein the semiconductor light emitter die is mounted on a first portion of the lead frame and the semiconductor light detector die is mounted on a second portion of the lead frame, wherein a third portion of the lead frame is interposed between the major emitter surface and the major detector surface, and the third portion of the lead frame is configured to attenuate or block substantially the transmission of undesired direct, scattered or reflected light between the major emitter surface and the major detector surface and thereby substantially avoid optical crosstalk and interference between the major emitter surface and the major detector surface, wherein at least portions of the semiconductor light emitter die and the semiconductor light detector die are separated by a gap, the gap corresponding to a void of material, the gap formed by extending a groove inwardly past at least one of the major emitter surface and the major detector surface to a base extremity of the groove.

* * * * *